US009775576B2

(12) United States Patent
Kassab et al.

(10) Patent No.: US 9,775,576 B2
(45) Date of Patent: *Oct. 3, 2017

(54) SYSTEMS AND METHODS FOR APPLYING SCALING LAWS OF TREE STRUCTURES

(71) Applicant: DTherapeutics, LLC, Zionsville, IN (US)

(72) Inventors: Ghassan S. Kassab, Zionsville, IN (US); Yunlong Huo, Beijing (CN)

(73) Assignee: DTherapeutics, LLC, San Diego, CA (US)

( * ) Notice: Subject to any disclaimer, the term of this patent is extended or adjusted under 35 U.S.C. 154(b) by 550 days.

This patent is subject to a terminal disclaimer.

(21) Appl. No.: 14/205,035

(22) Filed: Mar. 11, 2014

(65) Prior Publication Data

US 2014/0257078 A1 Sep. 11, 2014

Related U.S. Application Data

(63) Continuation of application No. 12/864,016, filed as application No. PCT/US2008/072925 on Aug. 12, 2008, now Pat. No. 8,670,943, which is a continuation-in-part of application No. PCT/US2008/000762, filed on Jan. 22, 2008.

(Continued)

(51) Int. Cl.
| | |
|---|---|
| *G06F 19/00* | (2011.01) |
| *A61B 5/00* | (2006.01) |
| *A61B 6/00* | (2006.01) |
| *A61B 5/02* | (2006.01) |
| *A61B 5/026* | (2006.01) |
| *A61B 5/055* | (2006.01) |
| *A61B 6/03* | (2006.01) |

(52) U.S. Cl.
CPC .............. *A61B 6/504* (2013.01); *A61B 5/026* (2013.01); *A61B 5/02007* (2013.01); *A61B 5/7246* (2013.01); *A61B 5/055* (2013.01); *A61B 6/03* (2013.01)

(58) Field of Classification Search
CPC ..... A61B 5/02007; A61B 5/026; A61B 5/055; A61B 5/7246; A61B 6/03; A61B 6/504
USPC .......... 702/19, 156, 157, 158; 600/420, 431, 600/454, 481, 508, 538; 703/11
See application file for complete search history.

(56) References Cited

U.S. PATENT DOCUMENTS

| | | |
|---|---|---|
| 5,958,202 A | 9/1999 | Regnier et al. |
| 6,042,208 A | 3/2000 | Wen |

(Continued)

OTHER PUBLICATIONS

Gabrys, et al. "Fractal models of circulatory system. Symmetrical and asymmetrical approach comparison." Chaos, Solitons and Fractals, 2005, pp. 707-715, vol. 24.

(Continued)

*Primary Examiner* — John H Le
(74) *Attorney, Agent, or Firm* — Reichel Stohry LLP; Mark C. Reichel; Natalie J. Dean

(57) ABSTRACT

Methods are provided for determining flow resistance within at least a portion of a vessel, whereby at least a partial biological tree image is obtained and resistance is calculated therefrom based upon at least the length of a defined vessel portion and a diameter of a stem vessel at a location proximal to a vessel crown. Methods are also provided for determining vessel volume, whereby at least a partial biological tree image is obtained and cumulative crown volume is calculated based on at least the diameter and length of the stem segment.

20 Claims, 21 Drawing Sheets

Related U.S. Application Data

(60) Provisional application No. 60/881,833, filed on Jan. 23, 2007.

(56) References Cited

U.S. PATENT DOCUMENTS

| | | | |
|---|---|---|---|
| 6,047,080 | A | 4/2000 | Chen et al. |
| 6,132,380 | A | 10/2000 | Cohen et al. |
| 6,221,226 | B1 | 4/2001 | Kopf-Sill |
| 6,260,021 | B1 | 7/2001 | Wong et al. |
| 6,261,233 | B1 | 7/2001 | Kantrovich |
| 6,500,323 | B1 | 12/2002 | Chow et al. |
| 6,537,799 | B2 | 3/2003 | Chow et al. |
| 7,069,068 | B1 | 6/2006 | Ostergaard |
| 7,452,726 | B2 | 11/2008 | Chou et al. |
| 7,775,083 | B2 | 8/2010 | Potyrailo et al. |
| 2003/0000835 | A1 | 1/2003 | Witt et al. |
| 2003/0200120 | A1 | 10/2003 | Binkert |
| 2005/0059876 | A1 | 3/2005 | Krishnan et al. |
| 2006/0004297 | A1 | 1/2006 | Orr et al. |
| 2006/0046300 | A1 | 3/2006 | Padmanabhan et al. |
| 2006/0235669 | A1 | 10/2006 | Charbel et al. |
| 2007/0026421 | A1 | 2/2007 | Sundberg et al. |
| 2007/0276270 | A1 | 11/2007 | Tran |
| 2008/0177518 | A1 | 7/2008 | Krishnamoorthy et al. |
| 2009/0036817 | A1 | 2/2009 | Dakin et al. |

OTHER PUBLICATIONS

Huo, et al. "A Scaling Law of Vascular Volume." Biophysical Journal, Jan. 2009, pp. 347-353, vol. 96.
Zhou, et al. "On the design of the coronary arterial tree: a generalization of Murray's law." Phys. Med. Biol., 1999, pp. 2929-2945, vol. 44.
Zhou, et al. "In vivo validation of the design rules of the coronary arteries and their application in the assessment of diffuse disease." Phys. Med. Biol., 2002, pp. 977-993.
International Searching Authority, International Search Report, PCT/US2008/000762, dated Aug. 29, 2008.
International Searching Authority, Written Opinion of the International Searching Authority, PCT/US2008/000762, dated Aug. 29, 2008.
International Searching Authority, International Search Report, PCT/US2008/072925, dated Dec. 1, 2008.
International Searching Authority, Written Opinion of the International Searching Authority, PCT/US2008/072925, dated Dec. 1, 2008.

| Species | Vessel (N) | $A_1$ | $R^2$ | $(K_s/K_c)_{ML}$ | $R^2$ |
|---|---|---|---|---|---|
| Pig | RCA (11) | 1.06 | 0.93 | 2.38 | 0.88 |
| Pig | LAD (11) | 1.02 | 0.99 | 5.32 | 0.97 |
| Pig | LCx (10) | 1.01 | 0.98 | 5.79 | 0.99 |
| Rat | PA (11) | 1.07 | 0.90 | 5.03 | 0.86 |
| Cat | PA (10) | 1.03 | 0.98 | 24.3 | 0.90 |
| Cat | PV (10) | 1.02 | 0.99 | 14.1 | 0.85 |
| Human | PA (17) | 0.97 | 0.98 | 2002 | 0.85 |
| Human | PA (15) | 0.98 | 0.98 | 1956 | 0.91 |
| Human | PA (17) | 0.95 | 0.97 | 445 | 0.80 |
| Human | PV (15) | 0.97 | 0.98 | 726 | 0.96 |
| Human | PV (15) | 0.94 | 0.95 | 96.3 | 0.95 |
| Hamster | SKMA (4) | 0.97 | 0.98 | 1.16 | 0.92 |
| Hamster | RMA (4) | 1.00 | 1.00 | 1.76 | 0.98 |
| Rat | MA (4) | 1.11 | 0.83 | 4.99 | 0.55 |
| Cat | SMA (4) | 1.04 | 0.96 | 6.66 | 0.61 |
| Human | BCA (5) | 1.11 | 0.88 | 7.40 | 0.60 |
| Human | BCV (5) | 1.10 | 0.86 | 2.35 | 0.54 |
| Rabbit | OV (4) | 0.88 | 0.90 | 3.11 | 0.68 |

Fig. 7A

| Entire Trees | Least-Square Fit | | Marquardt-Levenberg Method | | |
|---|---|---|---|---|---|
| | $B$ | $R^2$ | $A$ | SE | $R^2$ |
| Pig LAD | 1.07 | 1 | 1.02 | 0.006 | 0.998 |
| Pig LCx0 | 1.08 | 1 | 0.99 | 0.008 | 0.997 |
| Pig RCA | 1.08 | 1 | 0.99 | 0.014 | 0.989 |

| Epicardial Trees | Least-Square Fit | | Marquardt-Levenberg Method | | |
|---|---|---|---|---|---|
| | $B$ | $R^2$ | $A$ | SE | $R^2$ |
| Pig LAD | 1.07 | 0.995 | 0.95 | 0.008 | 0.996 |
| Pig LCx | 1.03 | 0.994 | 0.97 | 0.013 | 0.994 |
| Pig RCA | 1.08 | 0.990 | 1.02 | 0.019 | 0.986 |

Fig. 9

|  | Least-Square Fit | | Marquardt-Levenberg Method | | |
| --- | --- | --- | --- | --- | --- |
| Species (N) | $B$ | $R^2$ | $A$ | SE | $R^2$ |
| Pig RCA (11) | 1.09 | 0.999 | 1 | 0.003 | 1 |
| Pig LAD (11) | 1.10 | 0.999 | 1 | 0 | 1 |
| Pig LCx (10) | 1.13 | 0.999 | 1 | 0.001 | 1 |
| Rat PA (11) | 1.06 | 0.999 | 0.99 | 0.017 | 0.997 |
| Cat PA (10) | 1.11 | 0.996 | 1.01 | 0.013 | 0.999 |
| Cat PV (10) | 1.09 | 1 | 0.99 | 0.018 | 0.997 |
| Human PA (17) | 0.88 | 1 | 1 | 0.004 | 1 |
| Human PA (15) | 0.95 | 0.998 | 1.02 | 0.025 | 0.991 |
| Human PA (17) | 0.92 | 1 | 0.997 | 0.006 | 0.999 |
| Human PV (15) | 1.05 | 0.995 | 1.02 | 0.019 | 0.996 |
| Human PV (15) | 0.94 | 1 | 1.01 | 0.014 | 0.997 |
| Hamster SKMA (4) | 1.02 | 0.995 | 1.01 | 0.031 | 0.997 |
| Rat MA (4) | 1 | 1 | 1 | 0.007 | 1 |
| Rabbit OV (4) | 0.98 | 0.994 | 0.96 | 0.073 | 0.981 |
| Human BCA (5) | 0.98 | 1 | 1.01 | 0.015 | 0.999 |
| Human BCV (4) | 1.02 | 1 | 1 | 0.004 | 1 |
| Hamster RMA (4) | 1.03 | 0.977 | 1 | 0.014 | 0.999 |
| Cat SMA (4) | 0.95 | 1 | 1 | 0.012 | 1 |

Fig. 10

| Species | Diameter-Length | | | Volume-Length | | | Flow-Diameter | | | Volume-Diameter | | |
|---|---|---|---|---|---|---|---|---|---|---|---|---|
| | A | SE | $R^2$ | A | SE | $R^2$ | A | SE | $R^2$ | A | SE | $R^2$ |
| Pig RCA | 1.01 | 0.010 | 0.999 | 1 | 0.002 | 1 | 1 | 0.007 | 1 | 1 | 0.007 | 0.999 |
| Pig LAD | 1.02 | 0.019 | 0.996 | 1 | 0.003 | 1 | 0.99 | 0.017 | 0.997 | 1 | 0.01 | 0.999 |
| Pig LCx | 1 | 0.007 | 1 | 1 | 0.001 | 1 | 1 | 0.001 | 1 | 1 | 0.001 | 1 |
| Rat PA | 1.02 | 0.021 | 0.995 | 0.99 | 0.014 | 0.998 | 0.98 | 0.021 | 0.995 | 0.98 | 0.032 | 0.99 |
| Cat PA | 1 | 0.014 | 0.998 | 1.01 | 0.011 | 0.999 | 1.01 | 0.006 | 1 | 1.01 | 0.017 | 0.998 |
| Cat PV | 0.99 | 0.017 | 0.997 | 0.99 | 0.020 | 0.996 | 1.01 | 0.012 | 0.999 | 0.99 | 0.01 | 0.999 |
| Human PA | 0.92 | 0.037 | 0.977 | 1 | 0.006 | 0.999 | 1.02 | 0.034 | 0.982 | 1.01 | 0.022 | 0.993 |
| Human PA | 0.97 | 0.025 | 0.991 | 1.01 | 0.020 | 0.995 | 1.02 | 0.025 | 0.992 | 1.02 | 0.041 | 0.977 |
| Human PA | 0.90 | 0.041 | 0.973 | 0.99 | 0.014 | 0.997 | 1.03 | 0.041 | 0.974 | 1.01 | 0.021 | 0.993 |
| Human PV | 0.96 | 0.016 | 0.996 | 1.02 | 0.013 | 0.998 | 1.04 | 0.029 | 0.990 | 1.04 | 0.041 | 0.979 |
| Human PV | 0.88 | 0.054 | 0.955 | 1 | 0.001 | 1 | 1.02 | 0.053 | 0.963 | 1.01 | 0.041 | 0.976 |
| Hamster SKMA | 0.96 | 0.096 | 0.942 | 1 | 0.015 | 0.999 | 1.03 | 0.087 | 0.974 | 1.02 | 0.079 | 0.98 |
| Rat MA | 1.13 | 0.203 | 0.592 | 1.01 | 0.034 | 0.996 | 0.89 | 0.156 | 0.914 | 0.92 | 0.132 | 0.944 |
| Rabbit OV | 1.02 | 0.107 | 0.849 | 0.95 | 0.081 | 0.977 | 1.06 | 0.107 | 0.954 | 0.97 | 0.062 | 0.987 |
| Human BCA | 1.14 | 0.190 | 0.447 | 1.02 | 0.038 | 0.994 | 0.88 | 0.133 | 0.912 | 0.92 | 0.099 | 0.955 |
| Human BCV | 1.06 | 0.068 | 0.964 | 1 | 0.009 | 1 | 0.96 | 0.061 | 0.983 | 0.97 | 0.056 | 0.987 |
| Hamster RMA | 1.03 | 0.078 | 0.965 | 1 | 0.017 | 0.999 | 1.01 | 0.029 | 0.997 | 1 | 0.006 | 1 |
| Cat SMA | 1.11 | 0.193 | 0.633 | 1.01 | 0.034 | 0.996 | 0.92 | 0.133 | 0.938 | 0.95 | 0.103 | 0.966 |

Fig. 11

SYSTEMS AND METHODS FOR APPLYING SCALING LAWS OF TREE STRUCTURES

PRIORITY

The present application is related to, claims the priority benefit of, and is a U.S. continuation patent application of, U.S. patent application Ser. No. 12/864,016, filed on Jul. 22, 2010 and issued as U.S. Pat. No. 8,670,943 on Mar. 11, 2014, which is related to, claims the priority benefit of, and is a U.S. §371 National Stage Application of, International Patent Application Serial No. PCT/US2008/072925, filed Aug. 12, 2008, which is related to, claims the priority benefit of, and in some jurisdictions is considered a continuation-in-part application of, International Patent Application Serial No. PCT/US2008/000762, filed Jan. 22, 2008, which is related to, and claims the priority benefit of, U.S. Provisional Patent Application Ser. No. 60/881,833, filed Jan. 23, 2007. The contents of each of these applications and patent are hereby incorporated by reference in their entirety into this disclosure.

BACKGROUND

The disclosure of the present application relates generally to diagnosis of vascular disease, in particular relating to using morphological features of the coronary artery tree to diagnose coronary artery disease.

Diffuse coronary artery disease (DCAD), a common form of atherosclerosis, is difficult to diagnose because the arterial lumen cross-sectional area is diffusely reduced along the length of the vessels. Typically, for patients with even mild segmental stenosis, the lumen cross-sectional area is diffusely reduced by 30 to 50%. The failure of improved coronary flow reserve after angioplasty may mainly be due to the coexistence of diffuse narrowing and focal stenosis. Whereas angiography has been regarded as the "gold standard" in the assessment of focal stenosis of coronary arteries, its viability to diagnose DCAD remains questionable. The rationale of conventional angiography in the assessment of coronary artery disease is to calculate the percent lumen diameter reduction by comparison of the target segment with the adjacent 'normal' reference segment. In the presence of DCAD, however, an entire vessel may be diffusely narrowed so that no true reference (normal) segment exists. Therefore, in the presence of DCAD, standard angiography significantly underestimates the severity of the disease.

To overcome the difficulty of using angiography in the diagnosis of DCAD, intravascular ultrasound (IVUS) has been the subject of extensive studies. IVUS has the advantage of directly imaging the cross-sectional area along the length of the vessel using a small catheter. The disadvantage of IVUS, however, is that its extensive interrogation of diseased segments may pose a risk for plaque rupture.

In addition to the foregoing, biological transport structures (vascular trees, for example), have significant similarities despite remarkable diversity and size across species. The vascular tree, whose function is to transport fluid within an organism, is a major distribution system, which has known fractal and scaling characteristics. A fundamental functional parameter of a vessel segment or a tree is the hydraulic resistance to flow, which determines the transport efficiency. It is important to understand the hydraulic resistance of a vascular tree because it is the major determinant of transport in biology.

In a hydrodynamic analysis of mammalian and plant vascular networks, a mathematical model of ¾-power scaling for metabolic rates has been reported. A number of scaling relations of structure-function features were further proposed for body size, temperature, species abundance, body growth, and so on. Although the ¾ scaling law was originally derived through a hemodynamic analysis in the vascular tree system, at least one basic structure-function scaling feature of vascular trees remains unclear: "How does the resistance of a vessel branch scale with the equivalent resistance of the corresponding distal tree?"

What is needed is an improved approach to diagnosis and prognosis of vascular disease and its symptoms that avoid intrusive and expensive methods while improving accuracy and efficacy. Such an approach may include, for example, a novel scaling law of a single vessel resistance as relative to its corresponding distal tree.

Blood pressure and perfusion of an organ depend on a complex interplay between cardiac output, intravascular volume, and vasomotor tone, amongst others. The vascular system provides the basic architecture to transport the fluids while other physical, physiological, and chemical factors affect the intravascular volume to regulate the flow in the body. Although the intravascular volume can adapt to normal physical training, many diagnostic and treatment options depend on the estimation of the volume status of patients. For example, a recent study classified blood volume status as hypovolemic, normovolemic, and hypervolemic.

Heart failure results in an increase of intravascular volume (hypervolemia) in response to decreased cardiac output and renal hypoperfusion. Conversely, myocardial ischemia and infarct lead to a decrease of intravascular volume (hypovolemia) distal to an occluded coronary artery, and patients with postural tachycardia syndrome also show hypervolemia. Furthermore, patients of edematous disorders have been found to have abnormal blood volume. Currently, there is no noninvasive method to determine the blood volume in sub-organ, organs, organ system or organism. The disclosure of the present application provides a novel scaling law that provides the basis for determination of blood volume throughout the vasculature.

BRIEF SUMMARY

In at least one embodiment of a method for determining the resistance of a flow within at least a portion of a vessel of the disclosure of the present application, the method comprises the steps of obtaining a biological tree image showing a structure of at least part of a biological tree, identifying a length of a vessel portion and a diameter of a stem vessel proximal to the vessel crown from the biological tree image, and calculating resistance based upon at least the length of a vessel portion and a diameter of a stem vessel proximal to the vessel crown. In another embodiment, the step of calculating resistance is further based upon the use of a constant. In yet another embodiment, the resistance is a resistance of a stem segment, and wherein the length is a length of a stem. In an additional embodiment, the step of calculating the resistance of a stem segment is further based upon the use of a constant for the stem. In yet an additional embodiment, the constant for the stem is equivalent to one hundred and twenty eight multiplied by a fluid viscosity divided by pi, or a mathematical equivalent thereof.

In at least one embodiment of a method for determining the resistance of a flow within at least a portion of a vessel of the disclosure of the present application, the step of calculating the resistance of a stem segment is performed by dividing the length of a stem by the diameter of a stem vessel proximal to the vessel crown to the fourth power multiplied by a constant for the stem, or a mathematical equivalent thereof. In another embodiment, the constant for the stem is equivalent to one hundred and twenty eight multiplied by a fluid viscosity divided by pi, or a mathematical equivalent thereof. In yet another embodiment, the resistance is a resistance of a crown, and wherein the length is a crown length. In an additional embodiment, the crown length is determined by a sum of lengths of all or substantially all of the vessels in a crown. In yet an additional embodiment, the step of calculating the resistance of a crown is further based upon the use of a constant for the crown.

In at least one embodiment of a method for determining the resistance of a flow within at least a portion of a vessel of the disclosure of the present application, the constant for the crown is equivalent to a maximum resistance multiplied by a maximum diameter to the fourth power divided by a maximum length, or a mathematical equivalent thereof. In another embodiment, the step of calculating the resistance of a crown is performed by dividing the crown length by the diameter of a stem vessel proximal to the vessel crown to the fourth power multiplied by a constant, or a mathematical equivalent thereof. In yet another embodiment, the constant for the crown is equivalent to a maximum resistance multiplied by a maximum diameter to the fourth power divided by a maximum length, or a mathematical equivalent thereof. In an additional embodiment, in the constant for the crown is dependent upon a branching ratio, a diameter ratio, a total number of tree generations, and viscosity within a crown. In yet an additional embodiment, the resistance is a total resistance of the biological tree, and wherein the length is a cumulative biological tree vessel length.

In at least one embodiment of a method for determining the resistance of a flow within at least a portion of a vessel of the disclosure of the present application, the step of calculating the total resistance of the biological tree is further based upon the use of a constant for the crown. In another embodiment, the constant for the crown is equivalent to the total resistance of the biological tree multiplied by a most proximal stem diameter to the fourth power divided by a cumulative biological tree vessel length, or a mathematical equivalent thereof. In yet another embodiment, the step of calculating the total resistance of the biological tree is performed by dividing the cumulative biological tree vessel length by the diameter of a stem vessel proximal to the vessel crown to the fourth power multiplied by a constant, or a mathematical equivalent thereof. In an additional embodiment, the constant for the crown is equivalent to the total resistance of the biological tree multiplied by a most proximal stem diameter to the fourth power divided by a cumulative biological tree vessel length, or a mathematical equivalent thereof. In yet an additional embodiment, the resistance is the resistance of blood within a vessel portion.

In at least one embodiment of a method for determining the resistance of a flow within at least a portion of a vessel of the disclosure of the present application, the vessel portion comprises a vessel selected from the group consisting of a blood vessel, a bile duct, a lung, and a neuron. In another embodiment, the resistance is the resistance of a gas within a vessel portion. In yet another embodiment, the gas comprises breathable air, and wherein the vessel portion comprises a portion of a lung. In an additional embodiment, the method further comprises the step of comparing the calculated resistance to a calculated model resistance to determine the extent of vessel and/or organ disease. In yet an additional embodiment, the step of comparing the calculated resistance to the calculated model resistance is performed by graphically comparing calculated resistance data to model resistance calculation data to determine the extent of vessel and/or organ disease by identifying one or more graphical differences between said data.

In at least one embodiment of a method for determining the resistance of a flow within at least a portion of a vessel of the disclosure of the present application, the step of comparing the calculated resistance to the calculated model resistance is performed by comparing calculated resistance data to model resistance calculation data in table form to determine the extent of vessel and/or organ disease by identifying one or more numerically calculated differences between said data. In another embodiment, the resistance is a resistance of a stem segment, and wherein the length is a length of a stem, and the method further comprises the steps of identifying a crown length from the biological tree image, and calculating crown resistance based upon at least the length of a vessel portion and a diameter of a stem vessel proximal to the vessel crown. In yet another embodiment, the method further comprises the step of determining a resistance scaling relation, wherein the resistance scaling relation comprises a first component, a second component, and a third component, or a mathematical equivalent thereof. In an additional embodiment, the first component comprises the resistance of a stem segment divided by the crown resistance, wherein the second component comprises a constant for the stem divided by a constant for the crown, and wherein the third component comprises the length of a stem divided by the crown length, and wherein the first component equals the second component multiplied by the third component, or a mathematical equivalent thereof. In yet an additional embodiment, the resistance is a resistance of a crown, the length is a length of a stem, and the method further comprises the steps of identifying a cumulative biological tree vessel length from the biological tree image, identifying a most proximal stem diameter from the biological tree image, and calculating a total resistance of at least part of a biological tree based upon at least the cumulative biological tree vessel length and the most proximal stein diameter.

In at least one embodiment of a method for determining the resistance of a flow within at least a portion of a vessel of the disclosure of the present application, the step of calculating a total resistance further comprises the use of a known parameter. In another embodiment, the method further comprises the step of determining a resistance sealing relation, wherein the resistance scaling relation comprises a first component, a second component, and a third component, or a mathematical equivalent thereof. In yet another embodiment, the first component comprises the resistance of a crown divided by the total resistance, wherein the second component comprise the diameter of a stem vessel proximal to the vessel portion divided by the most proximal stem diameter, and wherein the third component comprises the length of a crown divided by the cumulative biological tree vessel length, and wherein the first component multiplied by the second component to the fourth power equals a known parameter multiplied by the third component, or a mathematical equivalent thereof. In an additional embodiment, the calculated resistance provides information useful for a diagnosis of a disease.

In at least one embodiment of a method for diagnosing disease in a patient's biological tree, the method comprises the steps of obtaining a model biological tree, obtaining a patient's biological tree image showing a vasculature of at least part of a patient's biological tree, identifying a length of a patient vessel portion and a diameter of a patient stem vessel proximal to the vessel crown from the patient's biological tree image, calculating model resistance based upon at least a length of a model vessel portion and a diameter of a model stem vessel proximal to the vessel crown from the model biological tree image, calculating patient resistance based upon at least the length of the patient vessel portion and the diameter of the patient stem vessel proximal to the vessel crown from the patient's biological tree image, and comparing the calculated model resistance to the calculated patient resistance to determine the extent of vessel and/or organ disease. In another embodiment, the steps of calculating model resistance and calculating patient resistance are further based upon the use of a constant. In yet another embodiment, the patient resistance is a resistance of a stem segment, and wherein the length of the patient vessel portion is a length of a stem. In an additional embodiment, the step of calculating the resistance of a stem segment is performed by dividing the length of a stem by the diameter of the patient stem vessel proximal to the vessel crown to the fourth power multiplied by a constant for the stem, or a mathematical equivalent thereof. In yet an additional embodiment, the constant for the stem is equivalent to one hundred and twenty eight multiplied by a fluid viscosity divided by pi, or a mathematical equivalent thereof.

In at least one embodiment of a method for diagnosing disease in a patient's biological tree, the patient resistance is a resistance of a crown, and wherein the length of the patient vessel portion is a crown length. In another embodiment, the step of calculating the resistance of a crown is further based upon the use of a constant for the crown. In yet another embodiment, the constant for the crown is equivalent to a maximum resistance multiplied by a maximum diameter to the fourth power divided by a maximum length, or a mathematical equivalent thereof. In an additional embodiment, the step of calculating the resistance of a crown is performed by dividing the crown length by the diameter of the patient stem vessel proximal to the vessel crown to the fourth power multiplied by a constant, or a mathematical equivalent thereof. In yet an additional embodiment, the patient resistance is a total resistance of the biological tree, and wherein the length of the patient vessel portion is a cumulative biological tree vessel length. In another embodiment, the step of calculating the total resistance of the biological tree is further based upon the use of a constant for the crown.

In at least one embodiment of a method for diagnosing disease in a patient's biological tree, the step of calculating the total resistance of the biological tree is performed by dividing the cumulative biological tree vessel length by the diameter of the patient stem vessel proximal to the vessel crown to the fourth power multiplied by a constant, or a mathematical equivalent thereof. In another embodiment, the patient resistance is the resistance of blood within a vessel portion. In yet another embodiment, the patient vessel portion comprises a vessel selected from the group consisting of a blood vessel, a bile duct, a lung, and a neuron. In an additional embodiment, the patient resistance is the resistance of a gas within a vessel portion. In yet an additional embodiment, the gas comprises breathable air, and wherein the vessel portion comprises a portion of a lung.

In at least one embodiment of a method for diagnosing disease in a patient's biological tree, the step of comparing the calculated model resistance to the calculated patient resistance is performed by graphically comparing patient resistance data to model resistance data to determine the extent of vessel and/or organ disease by identifying one or more graphical differences between said data. In another embodiment, the step of comparing calculated model resistance to the calculated patient resistance is performed by comparing patient resistance data to model resistance data in table form to determine the extent of vessel and/or organ disease by identifying one or more numerically calculated differences between said data. In yet another embodiment, the model biological tree is generated from a minimum energy hypothesis calculation.

In at least one embodiment of a method for determining vessel volume, the method comprises the steps of obtaining a biological tree image showing a structure of at least part of a biological tree, identifying a diameter of a stem segment and a length of a stem segment from the biological tree image, and calculating cumulative crown volume based upon at least the diameter of the stem segment and the length of the stein segment. In another embodiment, the step of calculating cumulative crown volume is further based upon the use of a constant. In yet another embodiment, the step of calculating cumulative crown volume is performed by multiplying a constant by a product of the diameter of a stem segment to the two-thirds power and the length of a stem segment, or a mathematical equivalent thereof. In an additional embodiment, the diameter of a stem segment is a most proximal stem diameter, wherein the length of a stem segment is a cumulative biological tree vessel length, and wherein the cumulative crown volume is a cumulative biological tree volume. In yet an additional embodiment, the step of calculating the cumulative biological tree volume is further based upon the use of a constant.

In at least one embodiment of a method for determining vessel volume, the step of calculating cumulative biological tree volume is performed by multiplying a constant by a product of the most proximal stem diameter to the two-thirds power and the cumulative biological tree vessel length, or a mathematical equivalent thereof. In another embodiment, the method further comprises the step of comparing the calculated cumulative crown volume to a calculated model cumulative crown volume to determine the extent of vessel and/or organ disease. In yet another embodiment, the step of comparing the calculated cumulative crown volume to the calculated model cumulative crown volume is performed by graphically comparing calculated cumulative crown volume data to calculated model cumulative crown volume data to determine the extent of vessel and/or organ disease by identifying one or more graphical differences between said data. In an additional embodiment, the step of comparing the calculated cumulative crown volume to the calculated model cumulative crown volume is performed by comparing calculated cumulative crown volume data to calculated model cumulative crown volume data in table form to determine the extent of vessel and/or organ disease by identifying one or more numerically calculated differences between said data. In yet an additional embodiment, the method further comprises the steps of identifying a most proximal stem diameter from the biological tree image, identifying a cumulative biological tree vessel length from the biological tree image, and calculating cumulative biological tree volume based upon at least the most proximal stem diameter and the cumulative biological tree vessel length.

In at least one embodiment of a method for determining vessel volume, the method further comprises the step of determining a structure-function scaling relation, wherein the structure-function scaling relation comprises a first component and a second component or a mathematical equivalent thereof. In another embodiment, the first component comprises the cumulative crown volume divided by the cumulative biological tree volume, and wherein the second component comprises the diameter of a stem segment divided by the most proximal stem diameter, and wherein the first component equals the second component to the third power, or a mathematical equivalent thereof. In yet another embodiment, the method further comprises the step of determining a non-dimensional structure-function scaling relation, wherein the non-dimensional structure-function scaling relation comprises a first component, a second component, and a third component, or a mathematical equivalent thereof. In an additional embodiment, the first component comprises the cumulative crown volume divided by the cumulative biological the volume, wherein the second component comprises the diameter of a stem segment divided by the most proximal stem diameter, wherein the third component comprises the length of a stem segment divided by the cumulative biological tree vessel length, and wherein the first component equals the second component to the two-thirds power multiplied by the third component, or a mathematical equivalent thereof. In yet an additional embodiment, the calculated cumulative crown volume provides information useful for a diagnosis of a disease.

In at least one embodiment of a method for diagnosing disease in a patient's biological tree, the method comprising the steps of obtaining a model biological tree, obtaining a patient's biological tree image showing a vasculature of at least part of a patient's biological tree, identifying a diameter of a patient stem segment and a length of a patient stem segment from the patient's biological tree image, calculating model cumulative crown volume based upon at least a diameter of a model stem segment and a length of a model stem segment from the model biological tree, calculating patient cumulative crown volume based upon at least the diameter of the patient stem segment and the length of the patient stem segment the patient's biological tree image, and comparing the calculated model cumulative crown volume to the calculated patient cumulative crown volume to determine the extent of vessel and/or organ disease. In another embodiment, the step of calculating patient cumulative crown volume is further based upon the use of a constant. In yet another embodiment, the step of calculating patient cumulative crown volume is performed by multiplying a constant by a product of the diameter of the patient stem segment to the two-thirds power and the length of the patient stem segment, or a mathematical equivalent thereof. In an additional embodiment, the diameter of the patient stem segment is a most proximal stem diameter, wherein the length of the patient stem segment is a cumulative biological tree vessel length, and wherein the patient cumulative crown volume is a cumulative biological tree volume. In yet an additional embodiment, the step of calculating the cumulative biological tree volume is further based upon the use of a constant.

In at least one embodiment of a method for diagnosing disease in a patient's biological tree, the step of calculating cumulative biological tree volume is performed by multiplying a constant by a product of the most proximal stem diameter to the two-thirds power and the cumulative biological tree vessel length, or a mathematical equivalent thereof. In another embodiment, the step of comparing the calculated model cumulative crown volume to the calculated model cumulative crown volume is performed by graphically comparing calculated model cumulative crown volume data to calculated model cumulative crown volume data to determine the extent of vessel and/or organ disease by identifying one or more graphical differences between said data. In yet another embodiment, the step of comparing the calculated model cumulative crown volume to the calculated model cumulative crown volume is performed by comparing calculated model cumulative crown volume data to calculated model cumulative crown volume data in table form to determine the extent of vessel and/or organ disease by identifying one or more numerically calculated differences between said data. In an additional embodiment, the method further comprises the steps of identifying a most proximal patient stem diameter from the patient's biological tree image, identifying a patient's cumulative biological tree vessel length from the patient's biological tree image, and calculating a patient's cumulative biological tree volume of the patient's biological tree based upon at least the most proximal patient stem diameter and the patient's cumulative biological tree vessel length. In yet an additional embodiment, the method further comprises the step of determining a structure-function scaling relation, wherein the structure-function scaling relation comprises a first component and a second component, or a mathematical equivalent thereof.

In at least one embodiment of a method for diagnosing disease in a patient's biological tree, the first component comprises the patient's cumulative crown volume divided by the patient's cumulative biological tree volume, and wherein the second component comprises the diameter of the patient stem segment divided by the most proximal patient stem diameter, and wherein the first component equals the second component to the third power, or a mathematical equivalent thereof. In another embodiment, the method further comprises the step of determining a non-dimensional structure-function scaling relation, wherein the non-dimensional structure-function scaling relation comprises a first component, a second component, and a third component, or a mathematical equivalent thereof. In yet another embodiment, the first component comprises the patient's cumulative crown volume divided by the patient's cumulative biological tree volume, wherein the second component comprises the diameter of the patient stem segment divided by the most proximal patient stem diameter, wherein the third component comprises the length of the patient stem segment divided by the patient's cumulative biological tree vessel length, and wherein the first component equals the second component to the two-thirds power multiplied by the third component, or a mathematical equivalent thereof. In an additional embodiment, the calculated patient's cumulative crown volume provides information useful for a diagnosis of a disease.

In at least one embodiment of a system for determining the resistance of a flow within at least a portion of a vessel, the system comprises a processor, a storage medium operably connected to the processor, the storage medium capable of receiving and storing data relative of measurements from a vasculature of a vessel, wherein the processor is operable to perform one or more steps of one or more of the aforementioned methods.

In at least one embodiment of a program having a plurality of program steps to be executed on a computer having a processor and a storage medium to analyze data relative of a vasculature of a vessel, the program is operable to perform one or more steps of one or more of the aforementioned methods.

BRIEF DESCRIPTION OF THE DRAWINGS

FIG. 7A shows a table of parameters with correlation coefficients calculated from the Marquardt-Levenberg algorithm for various species, according to at least one embodiment of the present disclosure;

FIG. 9 shows a table of parameters B and A in asymmetric coronary trees and corresponding epicardial trees with vessel diameters greater than 1 mm, according to at least one embodiment of the present disclosure;

FIG. 10 shows a table of parameters B and A in various organs, according to at least one embodiment of the present disclosure;

FIG. 11 shows a table of parameter A obtained from nonlinear regression in various organs, according to at least one embodiment of the present disclosure;

DETAILED DESCRIPTION

Figure 1:
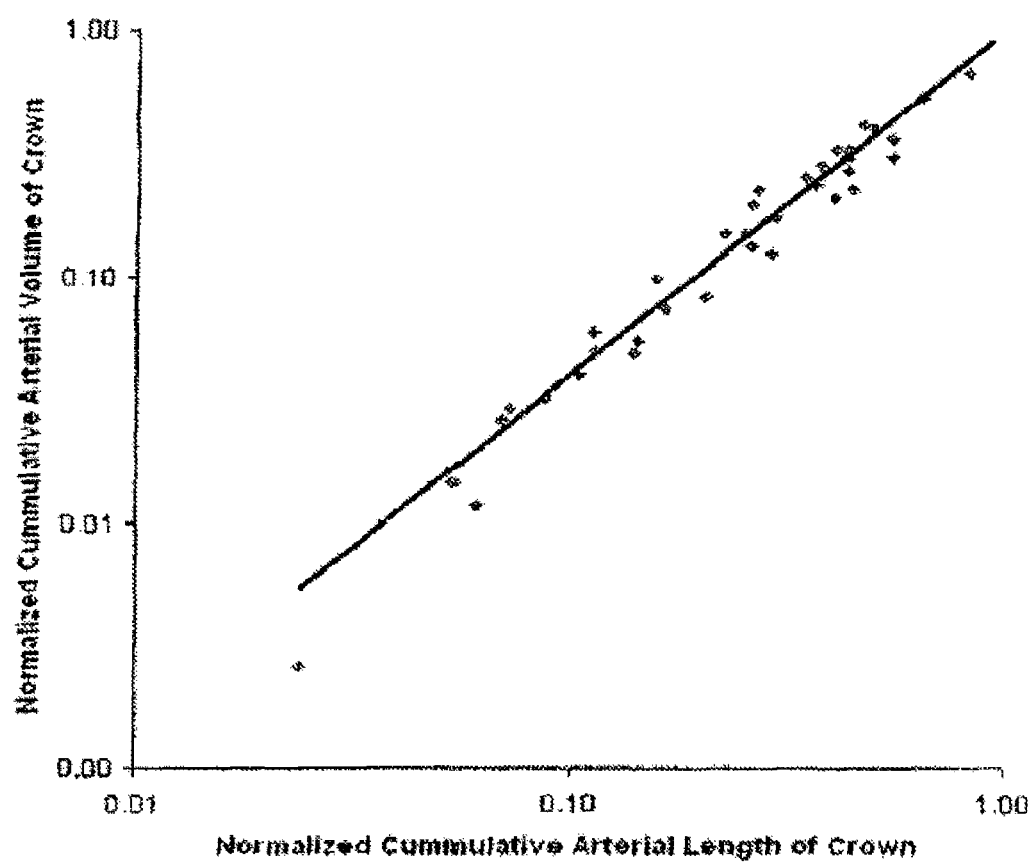
FIG. 1 shows the relation between normalized cumulative arterial volume and corresponding normalized cumulative arterial length for each crown on a log-log plot, according to at least one embodiment of the present disclosure.

The disclosure of the present application applies concepts from biomimetics and microfluidics to analyze vascular tree structure, thus improving the efficacy and accuracy of diagnostics involving vascular diseases such as DCAD. Scaling laws are developed in the form of equations that use the relationships between arterial volume, cross-sectional area, blood flow and the distal arterial length to quantify moderate levels of diffuse coronary artery disease. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

Biomimetics (also known as bionics, biognosis, biomimicry, or bionical creativity engineering) is defined as the application of methods and systems found in nature to the study and design of engineering systems and modern technology. The mimic of technology from nature is based on the premise that evolutionary pressure forces natural systems to become highly optimized and efficient. Some examples include (1) the development of dirt- and water-repellent paint from the observation that the surface of the lotus flower plant is practically unsticky, (2) hulls of boats imitating the thick skin of dolphins, and (3) sonar, radar, and medical ultrasound imaging imitating the echolocation of bats.

Microfluidics is the study of the behavior, control and manipulation of microliter and nanoliter volumes of fluids. It is a multidisciplinary field comprising physics, chemistry, engineering and biotechnology, with practical applications to the design of systems in which such small volumes of fluids may be used. Microfluidics is used in the development of DNA chips, micro-propulsion, micro-thermal technologies, and lab-on-a-chip technology.

Regarding the minimum energy hypothesis, the architecture (or manifolds) of the transport network is essential for transport of material in microfluid channels for various chips. The issue is how to design new devices, and more particularly, how to fabricate microfluidic channels that provide a minimum cost of operation. Nature has developed optimal channels (or transport systems) that utilize minimum energy for transport of fluids. The utility of nature's design of transport systems in engineering applications is an important area of biomimetics.

Biological trees (for example, vascular trees) are either used to conduct fluids such as blood, air, bile or urine. Energy expenditure is required for the conduction of fluid through a tree structure because of frictional losses. The frictional losses are reduced when the vessel branches have larger diameters. However, this comes with a cost associated with the metabolic construction and maintenance of the larger volume of the structure. The question is what physical or physiological factors dictate the design of vascular trees. The answer is that the design of vascular trees obeys the "minimum energy hypothesis", i.e., the cost of construction and operation of the vascular system appears to be optimized.

The disclosure of the present application is based on a set of scaling laws determined from a developed minimum energy hypothesis. Equation #1 (the "volume-length relation") demonstrates a relationship between vessel volume, the volume of the entire crown, vessel length, and the cumulative vessel length of the crown:

$$\frac{V}{V_{max}} = \left(\frac{L}{L_{max}}\right)^{\frac{5}{\varepsilon'+1}} \tag{1}$$

In Equation #1, V represents the vessel volume, $V_{max}$ the volume of the entire crown, L represents the vessel length, $L_{max}$ represents the cumulative vessel length of the entire crown, and $\epsilon'$ represents the crown flow resistance, which is equal to the ratio of metabolic to viscous power dissipation.

Equation #2 (the "diameter-length relation") demonstrates a relationship between vessel diameter, the diameter of the most proximal stem, vessel length, and the cumulative vessel length of the crown:

$$\frac{D}{D_{max}} = \left(\frac{L}{L_{max}}\right)^{\frac{3\epsilon'-2}{4(\epsilon'+1)}} \quad (2)$$

In Equation #2, D represents the vessel diameter, $D_{max}$ represents the diameter of the most proximal stem, L represents the vessel length, $L_{max}$ represents the cumulative vessel length of the entire crown, and $\epsilon'$ represents the crown flow resistance, which is equal to the ratio of metabolic to viscous power dissipation.

Equation #3 (the "flow rate-diameter relation") demonstrates a relationship between the flow rate of a stem, the flow rate of the most proximal stem, vessel diameter, and the diameter of the most proximal stem:

$$\frac{Q}{Q_{max}} = \left(\frac{D}{D_{max}}\right)^{\frac{4(\epsilon'+1)}{3\epsilon'-2}} \quad (3)$$

In Equation #3, Q represents flow rate of a stem, $Q_{max}$ represents the flow rate of the most proximal stein, V represents vessel diameter, $V_{max}$ represents the diameter of the most proximal stem, and $\epsilon'$ represents the crown flow resistance, which is equal to the ratio of metabolic to viscous power dissipation.

Regarding the aforementioned Equations, a vessel segment is referred to as a "stem," and the entire tree distal to the stem is referred as a "crown." The aforementioned parameters relate to the crown flow resistance and is equal to the ratio of maximum metabolic-to-viscous power dissipation.

Two additional relations were found for the vascular trees. Equation #4 (the "resistance-length and volume relation") demonstrates a relationship between the crown resistance, the resistance of the entire tree, vessel length, the cumulative vessel length of the crown, vessel volume, and the volume of the entire crown:

$$\frac{R_c}{R_{max}} = \frac{(L/L_{max})^3}{(V/V_{max})^{\epsilon'}} \quad (4)$$

In Equation #4, $R_c$ represents the crown resistance, $R_{max}$ represents the resistance of the entire tree, L represents vessel length, $L_{max}$ represents the cumulative vessel length of the entire crown, V represents vessel volume, $V_{max}$ represents the volume of the entire crown, and $\epsilon'$ represents the crown flow resistance, which is equal to the ratio of metabolic to viscous power dissipation. Resistance, as referenced herein, is defined as the ratio of pressure differenced between inlet and outlet of the vessel.

Equation #5 (the "flow rate-length relation") demonstrates a relationship between the flow rate of a stem, the flow rate of the most proximal stem, vessel length, the cumulative vessel length of the entire crown:

$$\frac{Q}{Q_{max}} = \frac{L}{L_{max}} \quad (5)$$

In Equation #5, Q represents flow rate of a stem, $Q_{max}$ represents the flow rate of the most proximal stein, L represents vessel length, and $L_{max}$ represents the cumulative vessel length of the entire crown.

In at least one embodiment of the disclosure of the present application, the application of one or more of the aforementioned Equations to acquired vessel data may be useful diagnose and/or aid in the diagnosis of disease.

By way of example, the application of one or more of the aforementioned Equations are useful to diagnose DCAD. For such a diagnosis, the applications of Equations #1-#3 may provide the "signatures" of normal vascular trees and impart a rationale for diagnosis of disease processes. The self-similar nature of these laws implies that the analysis can be carried out on a partial tree as obtained from an angiogram, a computed tomography (CT) scan, or an magnetic resonance imaging (MRI). Hence, the application of these Equations to the obtained images may serve for diagnosis of vascular disease that affect the lumen dimension, volume, length (vascularity) or perfusion (flow rate). Additionally, the fabrication of the microfluidic channels can be governed by Equations #1-#5 to yield a system that requires minimum energy of construction and operation. Hence, energy requirements will be at a minimum to transport the required microfluidics.

In one exemplary embodiment, the application of the volume-length relation (Equation #1) to actual obtained images is considered as shown in FIG. 1. First, images (angiograms in this example) of swine coronary allies were obtained. The application of Equation #1 on various volumes and lengths from the angiograms resulted in the individual data points shown within FIG. 1 (on a logarithmic scale). The line depicted within FIG. 1 represents the mean of the data points (the best fit) among the identified data points.

Figure 2:
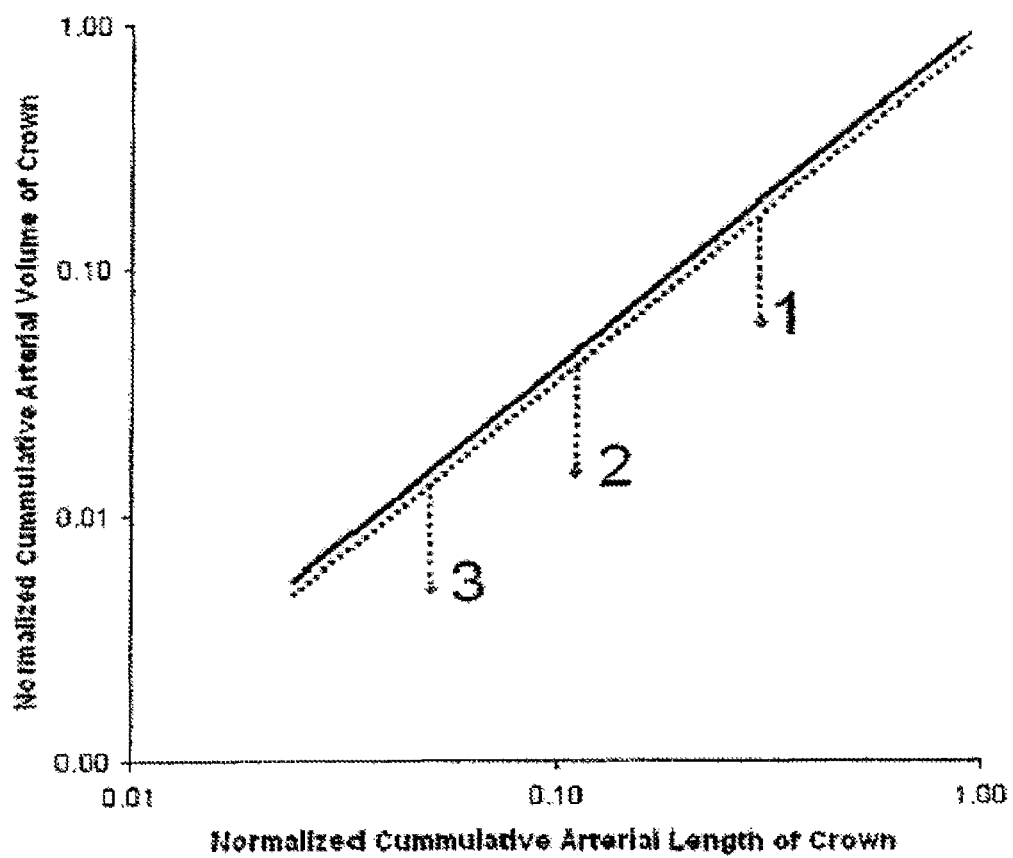
FIG. 2 shows the presence of DCAD at locations along the mean trend lines for normal (solid) and DCAD vasculature (broken) according to at least one embodiment of the present disclosure.

In FIG. 2, the mean of the data (solid line) is compared to an animal with diffuse disease at three different vessel sizes: proximal (1), middle (2), and distal (3). The reductions in volume shown on FIG. 2 correspond to approximately 40% stenosis, which is typically undetectable with current methodologies. At each diffuse stenosis, the length remains constant but the diameter (cross-sectional, and hence, volume) changes. The length is unlikely to change unless the flow becomes limiting (more than approximately 80% stenosis) and the vascular system experiences vessel loss (rarefication) and remodeling. It is clear that a 40% stenosis deviates significantly from the y-axis (as determined by statistical tests) from the normal vasculature, and as such, 40% stenosis can be diagnosed by the system and method of the disclosure of the present application. It can be appreciated that the disclosure of the present application can predict inefficiencies as low as about 10%, compared to well-trained clinicians who can only predict inefficiencies at about 60% at best.

This exemplary statistical test compares the deviation of disease to normality relative to the variation within normality. The location of the deviation along the x-axis corresponds to the size of the vessel. The vessel dimensions range as proximal>mid>distal. Hence, by utilizing the system and method of the disclosure of the present application, the diagnosis of the extent of disease and the dimension of the vessel branch is now possible. Similar embodiments with other scaling relations as described herein can be applied similarly to model and actual vascular data.

The techniques disclosed herein have tremendous application in a large number of technologies. For example, a software program or hardware device may be developed to diagnose the percentage of inefficiency (hence, occlusion) in a circulatory vessel or system.

Figure 3:
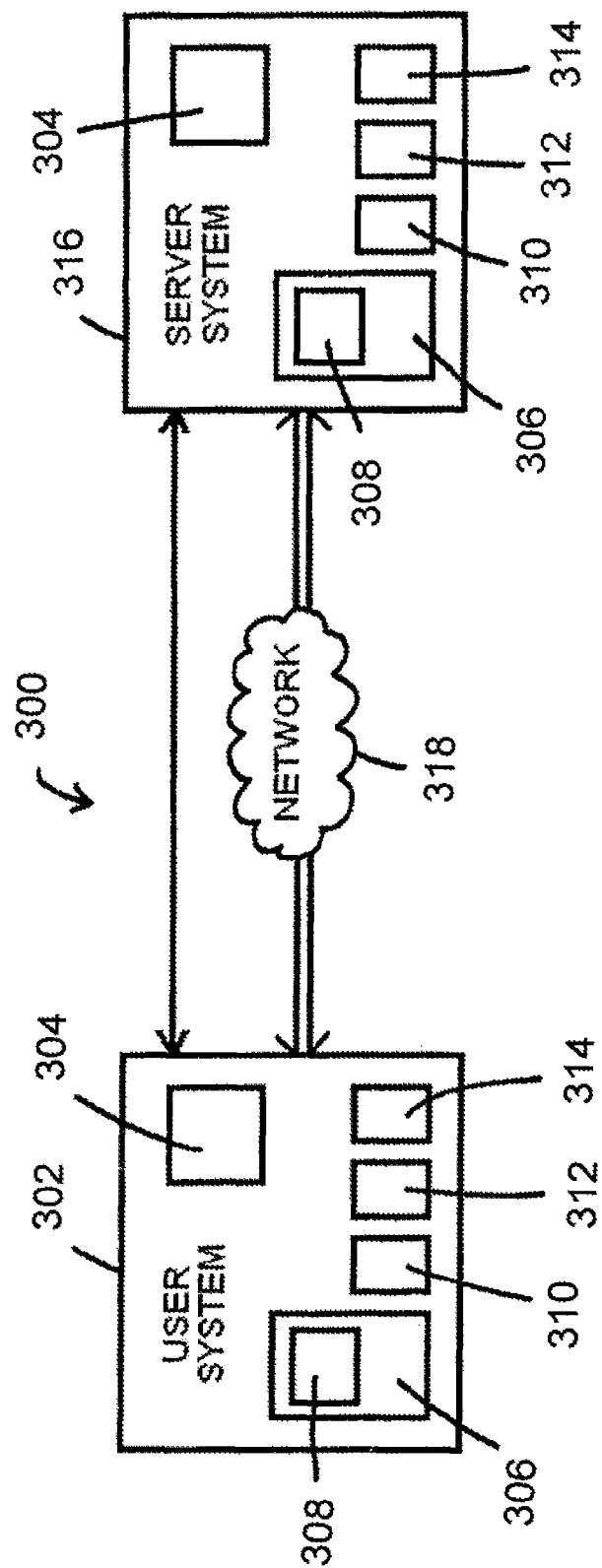
FIG. 3 shows a diagnostic system according to at least one embodiment of the present disclosure.

Regarding the computer-assisted determination of such diagnoses, an exemplary system of the disclosure of the present application is provided. Referring now to FIG. 3, there is shown a diagrammatic view of an embodiment of diagnostic system 300 of the present disclosure. In the embodiment shown in FIG. 3, diagnostic system 300 comprises user system 302. In this exemplary embodiment, user system 302 comprises processor 304 and one or more storage media 306. Processor 304 operates upon data obtained by or contained within user system 302. Storage medium 306 may contain database 308, whereby database 308 is capable of storing and retrieving data. Storage media 306 may contain a program (including, but not limited to, database 308), the program operable by processor 304 to perform a series of steps regarding data relative of vessel measurements as described in further detail herein.

Any number of storage media 306 may be used with diagnostic system 300 of the present disclosure, including, but not limited to, one or more of random access memory, read only memory, EPROMs, hard disk drives, floppy disk drives, optical disk drives, cartridge media, and smart cards, for example. As related to user system 302, storage media 306 may operate by storing data relative of vessel measurements for access by a user and/or for storing computer instructions. Processor 304 may also operate upon data stored within database 308.

Regardless of the embodiment of diagnostic system 300 referenced herein and/or contemplated to be within the scope of the present disclosure, each user system 302 may be of various configurations well known in the art. By way of example, user system 302, as shown in FIG. 3, comprises keyboard 310, monitor 312, and printer 314. Processor 304 may further operate to manage input and output from keyboard 310, monitor 312, and printer 314. Keyboard 310 is an exemplary input device, operating as a means for a user to input information to user system 302. Monitor 312 operates as a visual display means to display the data relative of vessel measurements and related information to a user using a user system 302. Printer 314 operates as a means to display data relative of vessel measurements and related information. Other input and output devices, such as a keypad, a computer mouse, a fingerprint reader, a pointing device, a microphone, and one or more loudspeakers are contemplated to be within the scope of the present disclosure. It can be appreciated that processor 304, keyboard 310, monitor 312, printer 314 and other input and output devices referenced herein may be components of one or more user systems 302 of the present disclosure.

It can be appreciated that diagnostic system 300 may further comprise one or more server systems 316 in bidirectional communication with user system 302, either by direct communication (shown by the single line connection on FIG. 3), or through a network 318 (shown by the double line connections on FIG. 3) by one of several configurations known in the art. Such server systems 316 may comprise one or more of the features of a user system 302 as described herein, including, but not limited to, processor 304, storage media 306, database 308, keyboard 310, monitor 312, and printer 314, as shown in the embodiment of diagnostic system 300 shown in FIG. 3. Such server systems 316 may allow bidirectional communication with one or more user systems 302 to allow user system 302 to access data relative of vessel measurements and related information from the server systems 316. It can be appreciated that a user system 302 and/or a server system 316 referenced herein may be generally referred to as a "computer."

Figure 4:
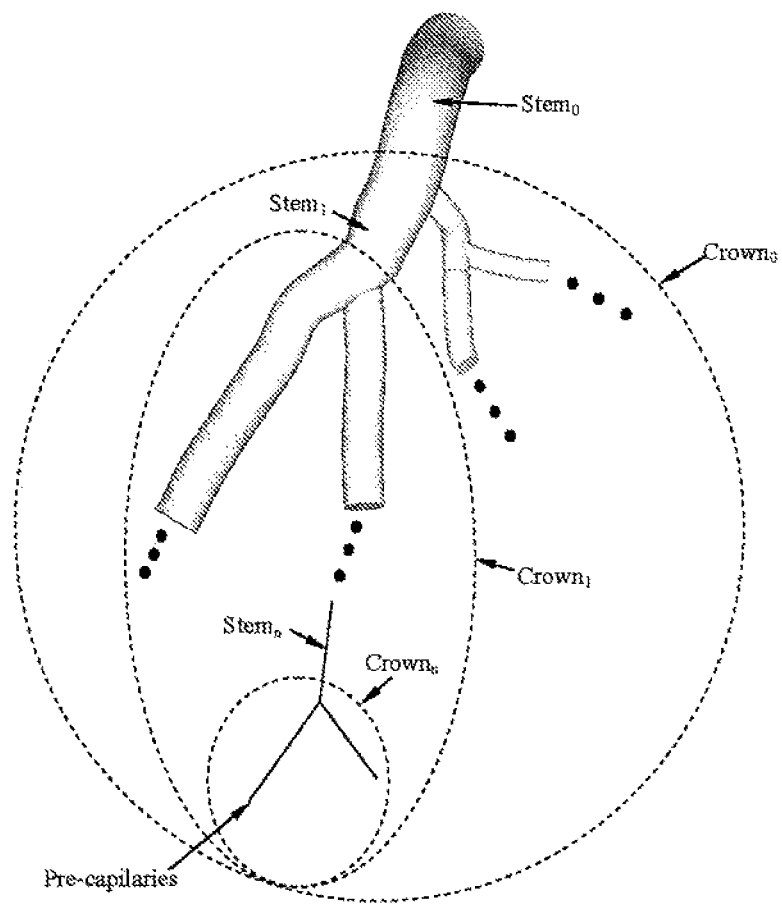
FIG. 4 shows an illustration of a definition of a stem-crown unit according to at least one embodiment of the present disclosure.

Several concepts are defined to formulate resistance scaling laws of the disclosure of the present application. A vessel segment is defined as a "stem" and the entire tree distal to the stem is defined as a "crown," as shown in FIG. 4 and as previously disclosed herein. FIG. 4 shows a schematic illustration of the definition of the stem-crown unit. Three stem-crown units are shown successively (1, 2, and n), with the smallest unit corresponding to an arteriole-capillary or venule-capillary unit. An entire vascular tree, or substantially the entire vascular tree, consists of many stem-crown units down to, for example, the smallest arterioles or venules. In one exemplary embodiment of the disclosure of the present application, the capillary network (referenced herein as having vessel diameters of less than 8 microns) is excluded from the analysis because it is not tree-like in structure. A stem, for purposes of simplification, is assumed to be a cylindrical tube with no consideration of vessel tapering and other nonlinear effects as they play a relatively minor role in determining the hemodynamics of the entire tree. However, the disclosure of the present application is not intended to be limited by the aforementioned capillary network exclusion and/or the aforementioned stem assumption.

Through the Hagen-Poiseuille law known in the art, the resistance of the steady laminar flow in a stem of an entire tree may be provided as shown in Equation #6

$$R_s = \frac{\Delta P_s}{Q_s} \tag{6}$$

In Equation #6, $R_s$ is the resistance of a stem segment, $\Delta P_s$ is the pressure gradient along the stem, and $Q_s$ is a volumetric flow rate through the stem.

According to the disclosure of the present application, Equation #6, providing for $R_s$ may be written in a form considering stem length and diameter, as shown in Equation #7.

$$R_s = \frac{128\mu L_s}{\pi D_s^4} = K_s \frac{L_s}{D_s^4} \tag{7}$$

In Equation #7, $R_s$ is the resistance of a stem segment, $L_s$ is the length of the stem, $D_s$ is the diameter of the stem, $\mu$ is the viscosity of a fluid, and $K_s$ is a constant equivalent to $128\mu/\pi$.

Furthermore, the resistance of a crown may be demonstrated as shown in Equation #8:

$$R_c = \frac{\Delta P_c}{Q_s} \tag{8}$$

In Equation #8, $R_c$ is the crown resistance, $\Delta P_s$ is the pressure gradient in the crown from the stem to the terminal vessels, and $Q_s$ is a volumetric flow rate through the stem Equation #8 may also be written in a novel form to solve for $R_c$ in accordance with the disclosure of the present application as shown in Equation #9:

$$R_c = K_c \frac{L_c}{D_s^4} \quad (9)$$

In Equation #9, $R_c$ is the crown resistance, $L_c$ is the crown length, $D_s$ is the diameter of the stem vessel proximal to the crown, and $K_c$ is a constant that depends on the branching ration, diameter ratio, the total number of tree generations, and viscosity in the crown. The crown length, $L_c$, may be defined as the sum of the lengths of each vessel in the crown (or substantially all of the vessels in the crown).

As Equation #9, according to the disclosure of the present application, is applicable to any stem-crown unit, one may obtain the following equation:

$$R_{max} = K_c \frac{L_{max}}{D_{max}^4} \quad (10)$$

so that the following formula for $K_c$ may be obtained:

$$K_c = \frac{R_{max} \cdot D_{max}^4}{L_{max}} \quad (11)$$

$D_{max}$, $L_{max}$, and $R_{max}$ correspond to the most proximal stem diameter, the cumulative vascular length, and total resistance of the entire tree, respectively. In the non-dimensional form, Equation #11 can be written as:

$$\left(\frac{R_c}{R_{max}}\right) \cdot \left(\frac{D_s}{D_{max}}\right)^4 = A_1 \left(\frac{L_c}{L_{max}}\right) \quad (12)$$

Parameter $A_1$ in Equation #12, as provided above, should be equal to one. From Equations #7 and #9, one may then obtain the desired resistance sealing relation between a single vessel (a stem) and the distal crown tree:

$$\left(\frac{R_s}{R_c}\right) = \frac{K_s}{K_c}\left(\frac{L_s}{L_c}\right) \quad (13)$$

Equations 47-13 relate the resistance of a single vessel to the corresponding distal tree.

Verification.

The asymmetric coronary arterial trees of hearts and symmetric vascular trees of many organs were used to verify the proposed resistance scaling law. First, the asymmetric coronary arterial tree has been reconstructed in pig hearts by using the growth algorithm introduced by Mittal et al, (A computer reconstruction of the entire coronary arterial tree based on detailed morphometric data. *Ann. Biomed. Eng.* 33 (8):1015-1026 (2005)) based on measured morphometric data of Kassab et al. (Morphometry of pig coronary arterial trees. *Am Physiol Heart Circ Physiol.* 265:H350-H365 (1993)). Briefly, vessels ≥40 μm were reconstructed from cast data while vessels <40 μm were reconstructed from histological data. After the tree was reconstructed, each vessel was assigned by diameter-defined Strahler orders which was developed based on the Strahler system (Strahler, A. N. Hypsometric (area altitude) analysis of erosional topology. *Bull Geol Soc Am.* 63:1117-1142 (1952)).

Furthermore, symmetric vascular trees of many organs were constructed in the Strahler system, based on the available literature. Here, the pulmonary arterial tree of rats was obtained from the study of Jiang et al. (Diameter-defined Strahler system and connectivity matrix of the pulmonary arterial tree. *J Appl. Physiol.* 76:882-892 (1994)); the pulmonary arterial/venous trees of cats from Yen et al. (Morphometry of cat's pulmonary arterial tree. *J. Biomech. Eng.* 106:131-136 (1984) and Morphometry of cat pulmonary venous tree. *J. Appl. Physiol. Respir. Environ. Exercise. Physiol.* 55:236-242 (1983)); the pulmonary arterial trees of humans from Singhal et al. (Morphometric study of pulmonary arterial tree and its hemodynamics. *J. Assoc. Physicians India.* 21:719-722 (1973) and Morphometry of the human pulmonary arterial tree. *Circ. Res.* 33:190 (1973)) and Huang et al. (Morphometry of the human pulmonary vasculature. *J. Appl. Physiol.* 81:2123-2133 (1996)); the pulmonary venous trees of humans from Horsfield et al. (Morphometry of pulmonary veins in man. *Lung.* 159:211-218 (1981)) and Huang et al.; the skin muscle arterial tree of hamsters from Bertuglia et al. (Hypoxia- or hyperoxia-induced changes in arteriolar vasomotion in skeletal muscle microcirculation. *Am J Physiol Heart Circ Physiol.* 260: H362-H372 (1991)); the retractor muscle arterial tree of hamsters from Ellsworth et al, (Analysis of vascular pattern and dimensions in arteriolar networks of the retractor muscle in young hamsters. *Microvasc. Res.* 34:168-183 (1987)); the mesentery arterial tree of rats from Ley et al. (Topological structure of rat mesenteric microvessel networks. *Microvasc. Res.* 32:315-332 (1986)); the sartorius muscle arterial tree of cats from Koller et al. (Quantitative analysis of arteriolar network architecture in cat sartorius muscle. *Am J Physiol. Heart Circ Physiol.* 253: H154-H164 (1987)); and the bulbular conjunctiva arterial/venous trees of humans and the omentum arterial tree of rabbits from Fenton et al. (Microcirculatory model relating geometrical variation to changes in pressure and flow rate. *Ann. Biomed. Eng.* 1981; 9:303-321 (1981)).

Data Analysis.

For the asymmetric coronary arterial trees, full tree data are presented as log-log density plots showing the frequency of data because of the enormity of data points, i.e., darkest shade reflects highest frequency or density and the lightest shade reflects the lowest frequency. The nonlinear regression (SigmaStat 3.5) is used to analyze the data in both asymmetric and symmetric tree, which uses the Marquardt-Levenberg algorithm (nonlinear regression) to find the coefficients (parameters) of the independent variables that give the "best fit" between the equation and the data.

Results: Validation of Resistance Scaling Law in Entire Vascular Trees.

The predictions of these novel scaling laws were then validated in both the asymmetric coronary trees and the symmetric vascular trees for which there exists morphometric data in the literature (e.g., vessels of various skeletal muscles, mesentery, omentum, and conjunctiva).

Figure 5A:
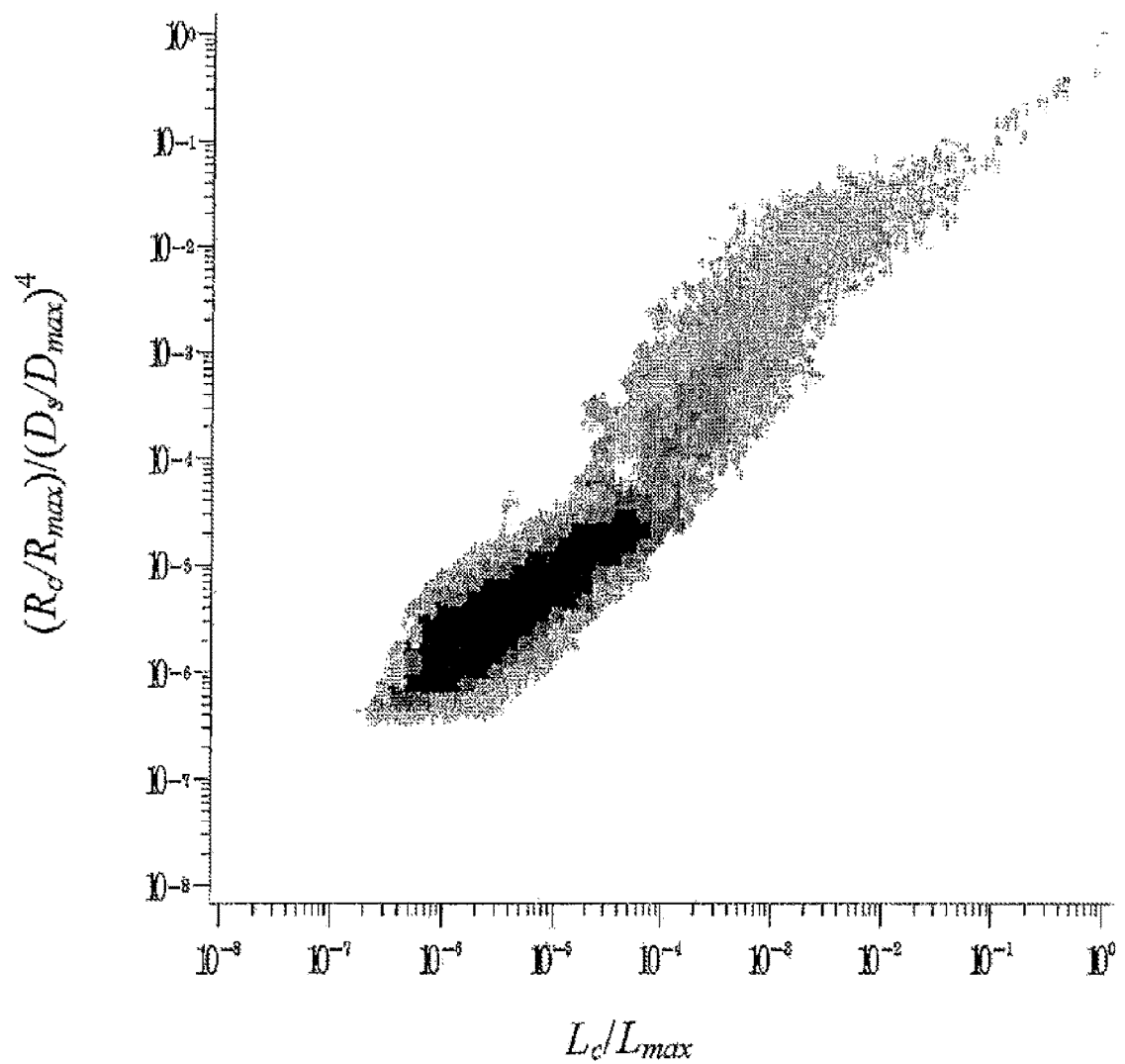
FIGS. 5A-5C show relationships between resistance and diameter and normalized crown length of LAD, LCx, and RCA trees of a pig, respectively, according to at least one embodiment of the present disclosure.
Figure 5B:
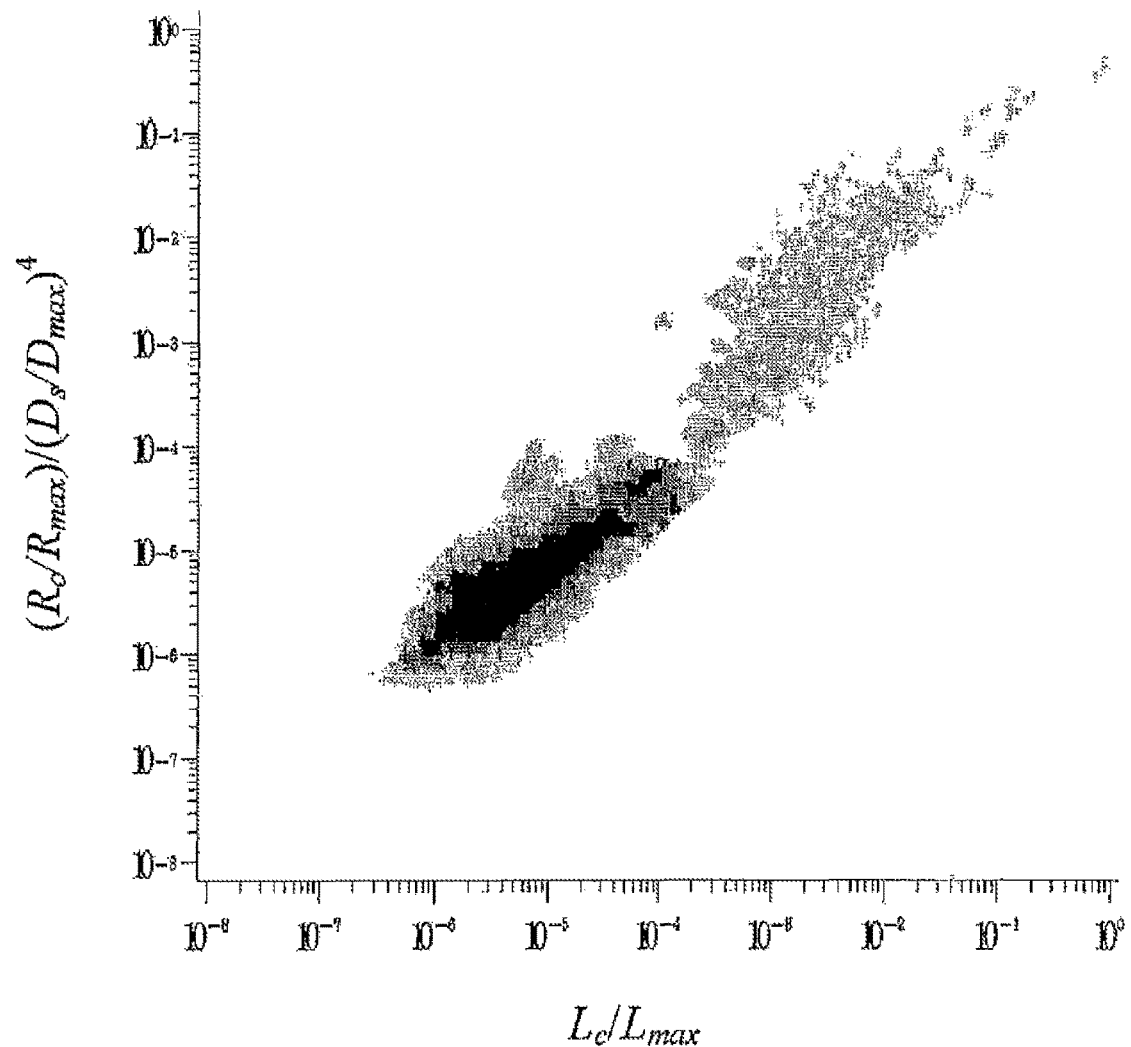
Figure 5C:
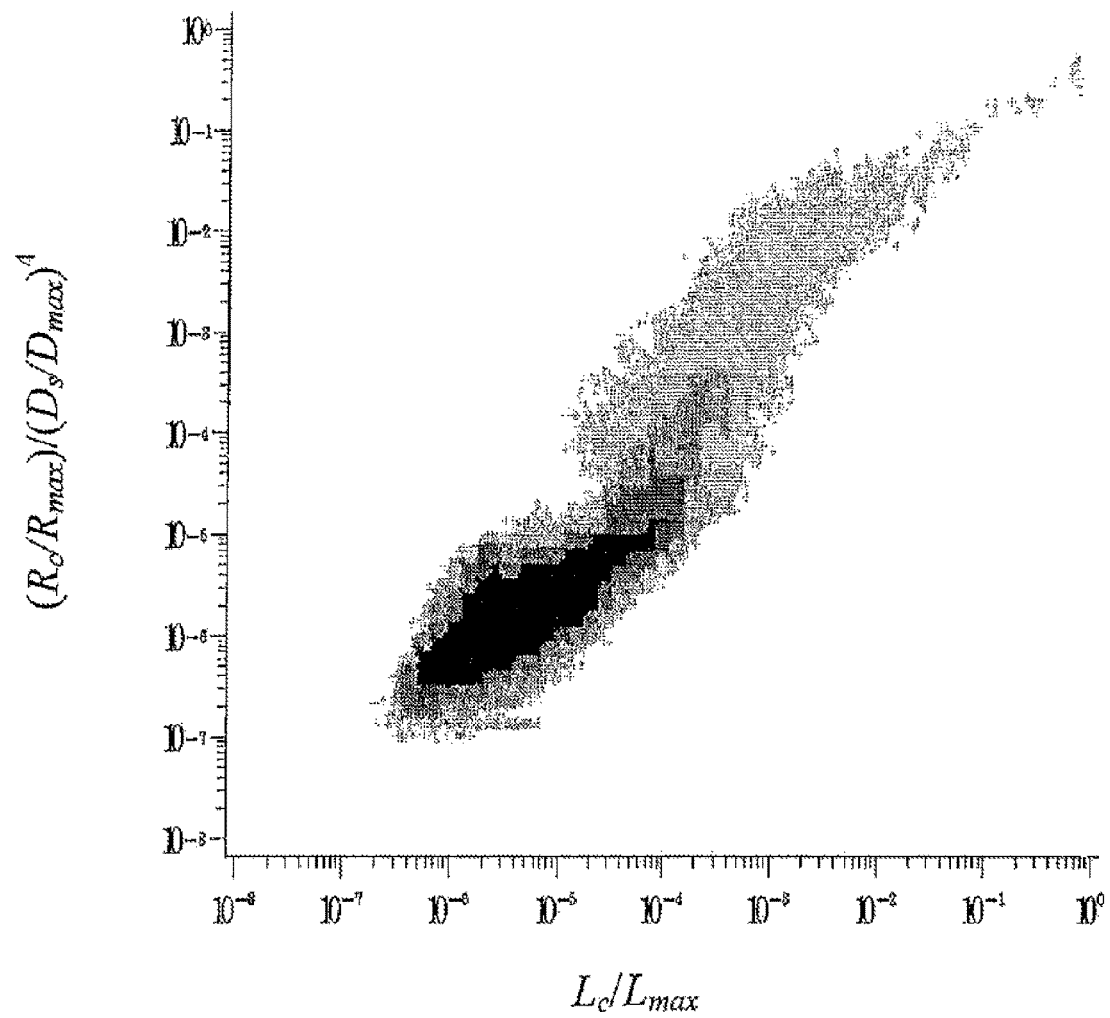
Figure 5D:
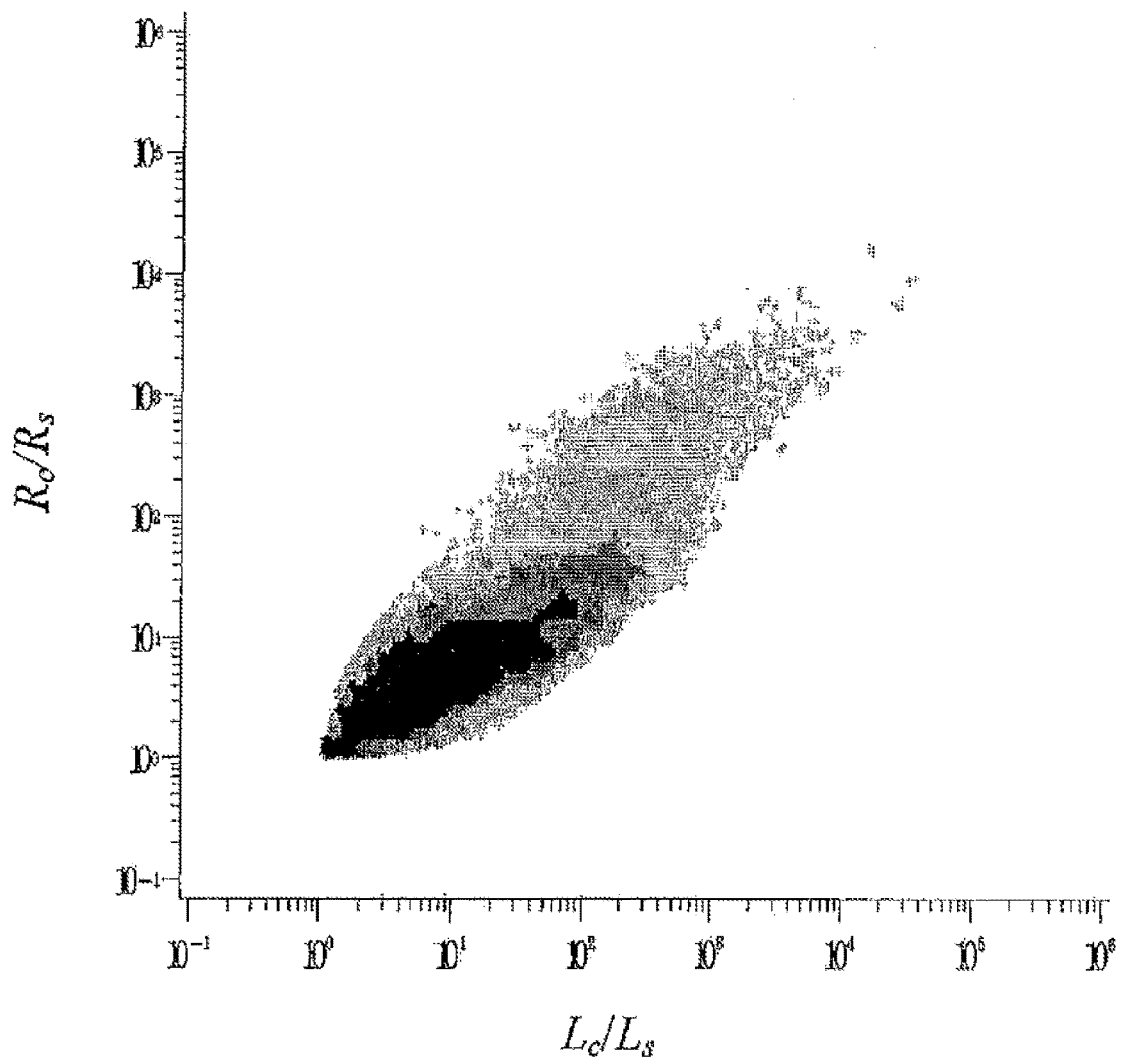
FIGS. 5D-5F show relationships between resistance and length of LAD, LCx, and RCA trees of a pig, respectively, according to at least one embodiment of the present disclosure.
Figure 5E:
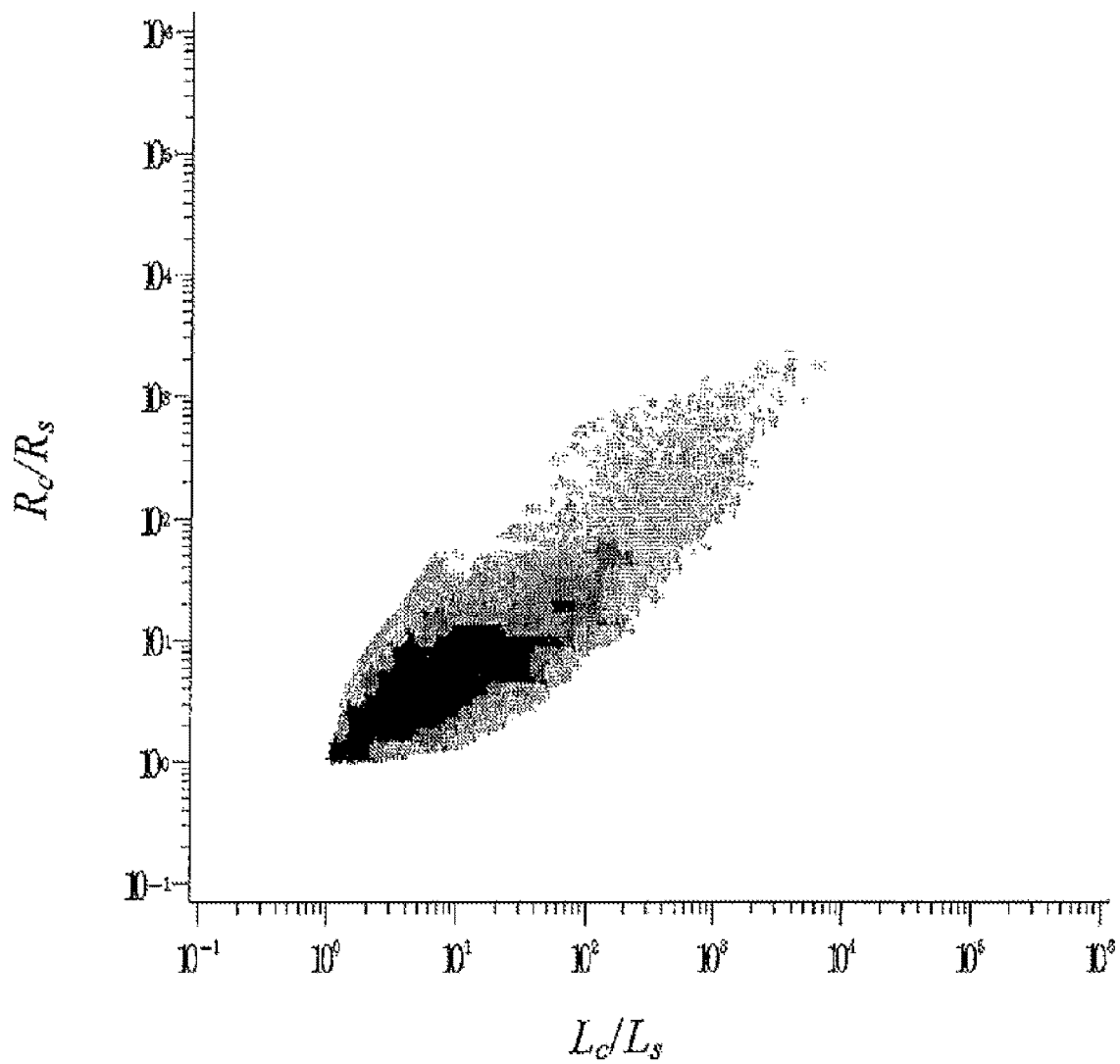
Figure 5F:
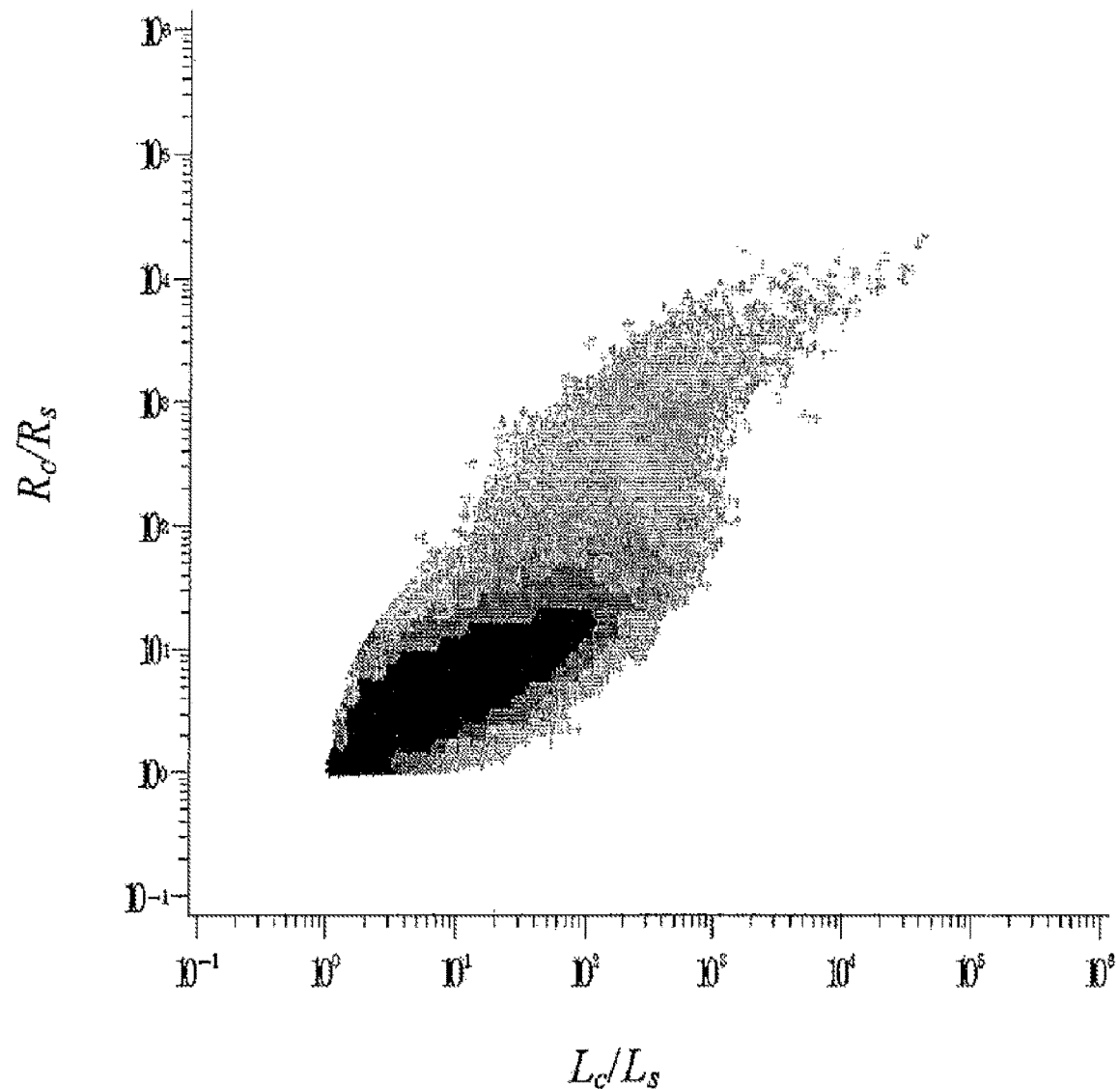

First, the entire asymmetric coronary LAD, LCx, and RCA trees with several millions of vessels were analyzed (15, 16). FIGS. 5A, 5B, and 5C show a log-log plot of $(R_c/R_{max}) \cdot (D_s/D_{max})^4$ as a function of normalized crown length $(L_c/L_{max})$ for LAD, LCx, and RCA trees, respectively. Relationships between $(R_c/R_{max}) \cdot (D_s/D_{max})^4$ and normalized crown length $(L_c/L_{max})$ in the asymmetric entire LAD (FIG. 5A), LCx (FIG. 5B), and RCA (FIG. 5C) trees of pig, which include 946937, 571383, and 836712 stem-crown units are shown, respectively. Through the Marquardt-Levenberg algorithm with the exponents of $L_c/L_{max}$ constrained to one, parameter $A_1$ in Equation #12 has a value of 1.027 ($R^2$=0.990), 0.993 ($R^2$=0.997), and 1.084 ($R^2$=0.975) for LAD, LCx, and RCA trees, respectively. The values of $A_1$ obtained from morphometric data are in agreement with the theoretical value of one. Corresponding to FIGS. 5A, 5B, and 5C, FIGS. 5D, 5E, and 5F show a log-log plot of $R_s/R_s$ as a function of $L_c/L_s$. Parameter $K_s/K_c$ in Equation #13 has a value of 2.647 ($R^2$=0.954), 2.943 ($R^2$=0.918), and 2.147 ($R^2$=0.909) for LAD, LCx, and RCA trees, respectively. FIGS. 5D, 5F, and 5F show a relationship between $R_c/R_s$ and $L_c/L_s$ in the LAD, LCx, and RCA trees of pig, corresponding to FIGS. 5A, 5B, and 5C.

Figure 6:
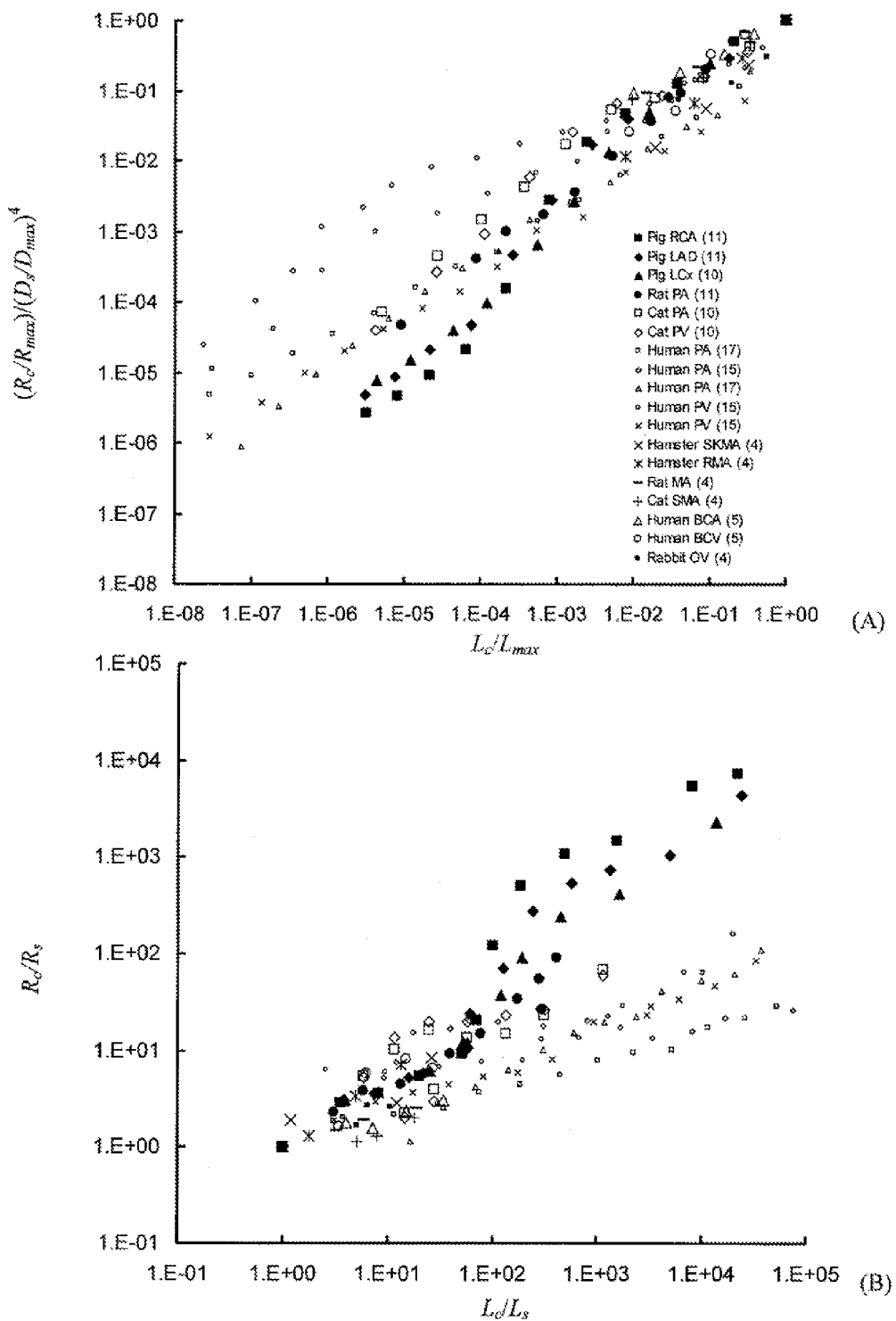
FIG. 6A shows a relationship between resistance and diameter and normalized crown length in symmetric vascular trees for various species, according to at least one embodiment of the present disclosure.
FIG. 6B shows a relationship between resistance and length in symmetric vascular trees for various species, according to at least one embodiment of the present disclosure.
Figure 7B:
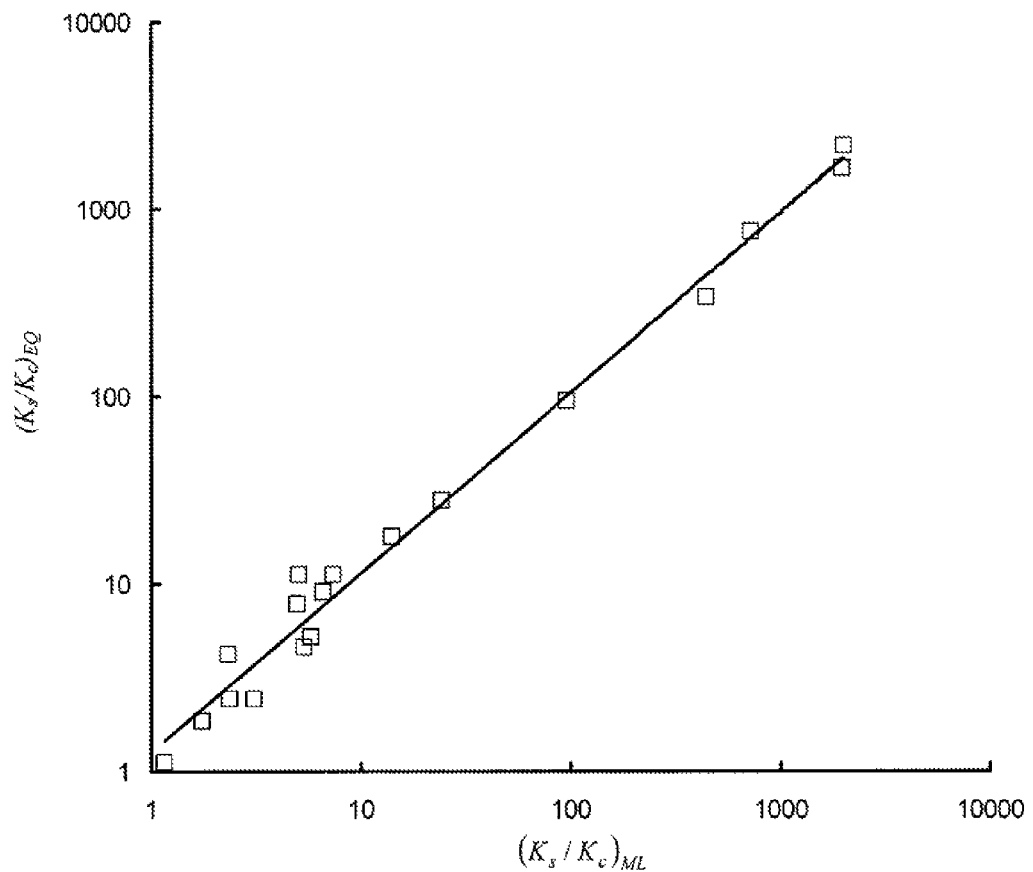
FIG. 7B shows a comparison of data from nonlinear regression and equations of the present disclosure; according to at least one embodiment of the present disclosure.

Furthermore, FIGS. 6A and 6B show the log-log plots of $(R_c/R_{max})\cdot(D_0/D_{max})^4$ and $R_c/R_s$ as a function of $L_c/L_{max}$ and $L_c/L_s$, respectively, in the vascular trees of various species. Corresponding to FIGS. 6A and 6B, the Marquardt-Levenherg algorithm was used to calculate the parameters $A_1$ and $K_s/K_c$ in Equations #12 and #13, respectively, while the exponents of $L_c/L_{max}$ and $L_c/L_s$ were constrained to be one. Parameters $A_1$ in Equation #12 and $K_s/K_c$ in Equation #13 with correlation coefficient for various species are listed in the table shown in FIG. 7A. The data in FIG. 7A have a mean value (averaged over all organs and species) of 1.01±0.06 for parameter $A_1$. FIG. 7B shows a comparison of $(K_s/K_c)_{ML}$ from the nonlinear regression of anatomical data and $(K_s/K_c)_{EQ}$ based on Equations $K_s$=128μ/π and $$K_c = \frac{R_{max} \cdot D_{max}^4}{L_{max}},$$

noting that the comparison can be represented as $$\left(\frac{K_s}{K_c}\right)_{EQ} = A \cdot \left(\frac{K_s}{K_c}\right)_{ML}^B.$$

When A is constrained to be one in the Marquardt-Levenberg algorithm, B has a value of one ($R^2$=0.983). Using the same Marquardt-Levenberg algorithm, a nonlinear regression fit of all raw data yields a mean of 1.01 ($R^2$=0.95) tier parameter $A_1$. Both the mean value and the nonlinear regression fit of all data agree with the theoretical value of one.

FIG. 6B shows much smaller $R_c/R_s$ in pulmonary vascular tree than other organs at the same value of $L_c/L_s$. Accordingly, the $K_s/K_c$ values (shown in the table in FIG. 7A) are similar except for the pulmonary vasculature with a larger value. The $K_s/K_c$ values are also calculated based on Equations $K_s$=128μ/π and $K_c$=$R_{max} \cdot D_{max}^4/L_{max}$, which is compared with the $K_s/K_c$ values obtained from the Marquardt-Levenberg algorithm, as shown in FIG. 7B. The viscosity is determined based on an empirical in vivo relation that depends on the vessel diameter. The comparison shows good agreement. The $K_s/K_c$ values in the pulmonary vasculature have a larger value because the cross-section area of pulmonary tree has a large increase from proximal to terminal vessels in the pulmonary tree and the resistance of the entire tree ($R_{max}$) is much smaller. The agreement between experimental measurement and theoretical relations illustrate that the novel resistance scaling law disclosed herein of Equations #9, #12, and #13 can be applied to a general vascular tree down to the smallest arterioles or venules.

Results: Resistance Scaling Law of Partial Vascular Trees.

FIGS. 8A and 8B show the relations between $(R_c/R_{max}) \cdot (D_s/D_{max})^4$ and normalized crown volume $(L_c/L_{max})$ and between $R_c/R_s$ and $L_c/L_s$, respectively, in the LAD, LCx, and RCA epicardial trees. FIG. 8A shows a relationship between $(R_c/R_{max}) \cdot (D_s/D_{max})^4$ and normalized crown volume $(L_c/L_{max})$ in the LAD, LCx, and RCA epicardial trees of pig with diameter of mother vessels larger than 1 mm, which include 132, 90, and 192 vessel segments, respectively. FIG. 8B shows a relationship between $R_c/R_s$ and $L_c/L_s$ in the LAD, LCx, and RCA epicardial trees of pig corresponding to FIG. 8A. Parameter $A_1$ in Equation #12 has a value of 0.902 ($R^2$=0.907), 0.895 ($R^2$=0.887), and 1.000 ($R^2$=0.888) and parameter $K_s/K_c$ in Equation #13 has a value of 3.29 ($R^2$=0.875), 3.48 ($R^2$=0.816), and 3.12 ($R^2$=0.927) for the LAD, LCx, and RCA epicardial trees, respectively.

The aforementioned study validates the novel resistance scaling law of the present disclosure that relates the resistance of a vessel branch to the equivalent resistance of the corresponding distal tree in various vascular trees of different organs and species. The significance of the resistant scaling law is that the hydraulic resistance of a distal vascular tree can be estimated from the proximal vessel segment. As a result, the disclosure of the present application has wide implications from understanding fundamental vascular design to diagnosis of disease in the vascular system.

Resistance Scaling Law.

The mechanisms responsible for blood flow regulation in vascular trees are of central importance, but are still poorly understood. The arteriolar beds are the major site of vascular resistance, which contributes to the maintenance and regulation of regional blood flow. Although arteriolar resistance plays an important role in the etiology of many diseases, in particular, hypertension, it has been difficult to predict the resistance in the arteriolar beds. The novel resistance scaling law of the present disclosure addresses this issue.

The resistance scaling laws (Equations #9, #12, and #13) are derived based on the relation of diameter ratio ($DR=D_i/D_{i-1}$), length ratio ($LR=L_i/L_{i-1}$) and branching ratio ($BR=N_i/N_{i-1}$) in a symmetric tree as:

$$DR = BR^{-\frac{1}{2+\varepsilon}} \text{ and } LR = BR^{-\frac{1}{3}},$$

where $\varepsilon$=0 and $\varepsilon$=1 represent the area-preservation, $\pi D_{i-1}^2 = BR \cdot \pi D_i^2$, and Murray's law, $\pi D_{i-1}^3 = BR \cdot \pi D_i^3$, respectively, Although the total cross-sectional area (CSA) may increase dramatically from the aorta to the arterioles, the variation is significantly smaller in most organs except for the lung. The increase of CSA towards the capillaries is typically inferred from the decrease in velocity. The velocity between the most proximal and distal levels in various organs of mammals is found to vary by about a factor of five, except for the pulmonary vascular trees. This is clearly reflected by the table shown in FIG. 7A, in which $$K_s/K_c = \frac{1}{K_\varepsilon}$$

is relatively small except for the pulmonary vasculature. This implies that wall shear stress (WSS) increases from the arteries to the arterioles in most organs, which is consistent with previous measurements.

Structure-Function Scaling Laws Obtained from Resistance Scaling Law.

A mathematical model (the ¾-power scaling law) was derived in a symmetric vasculature to characterize the allometric scaling laws, based on the minimum energy theory. The ¾-power scaling law can be written as $Q_s \propto M^{3/4}$, where $Q_s$ is the volumetric flow rate of the aorta and M is body mass. In a stein-crown unit, $Q_s$ is the volumetric flow rate of the stem and M is the mass perfused by the stem crown unit. The volumetric flow rate of the stem is $Q_s = \pi D_s^2 U_s/4$, where $D_s$ and $U_s$ are the diameter and the mean flow velocity of the stem (averaged over the cross-section of stem). Similar to at least one known model, the pressure drop from the stem to the capillaries ($\Delta P_c$) and the mean flow velocity of the stem ($U_s$) are independent of the perfused mass so that $D_s \propto M^{3/8}$ and the resistance of the crown ($R_c = \Delta P_c/Q_s$) is inversely proportional to the volumetric flow rate ($R_c \propto Q_s^{-1} \propto M^{-3/4}$). Since $D_s \propto M^{3/8}$, $R_c \propto M^{-3/4}$, and $K_c$, is a constant, Equations #9 and #12 yields that the crown length $L_c \propto M^{3/4}$. The cumulative length-mass scaling in pig hearts, $L_c \propto M^{3/4}$, has recently been verified by the present inventors and their research group. This relation, in conjunction with the flow-mass relation ($Q_s \propto M^{3/4}$), yields the flow-length relation ($Q_s \propto L_c$) in the stem-crown unit, which has been previously validated.

Here, the crown length $L_c \propto M^{3/4}$ is different from the biological length $l \propto M^{1/4}$. The biological length (l) is the cumulative length along a path from inlet (level zero) to the terminal (level N), but the crown length is the total length of all vessels from inlet to the terminals. Although the biological length shows that the vascular physiology and anatomy are four-dimensional, the crown length depicts a ¾-power relation between the total length of entire/partial biological system and the perfused mass.

Figure 8:
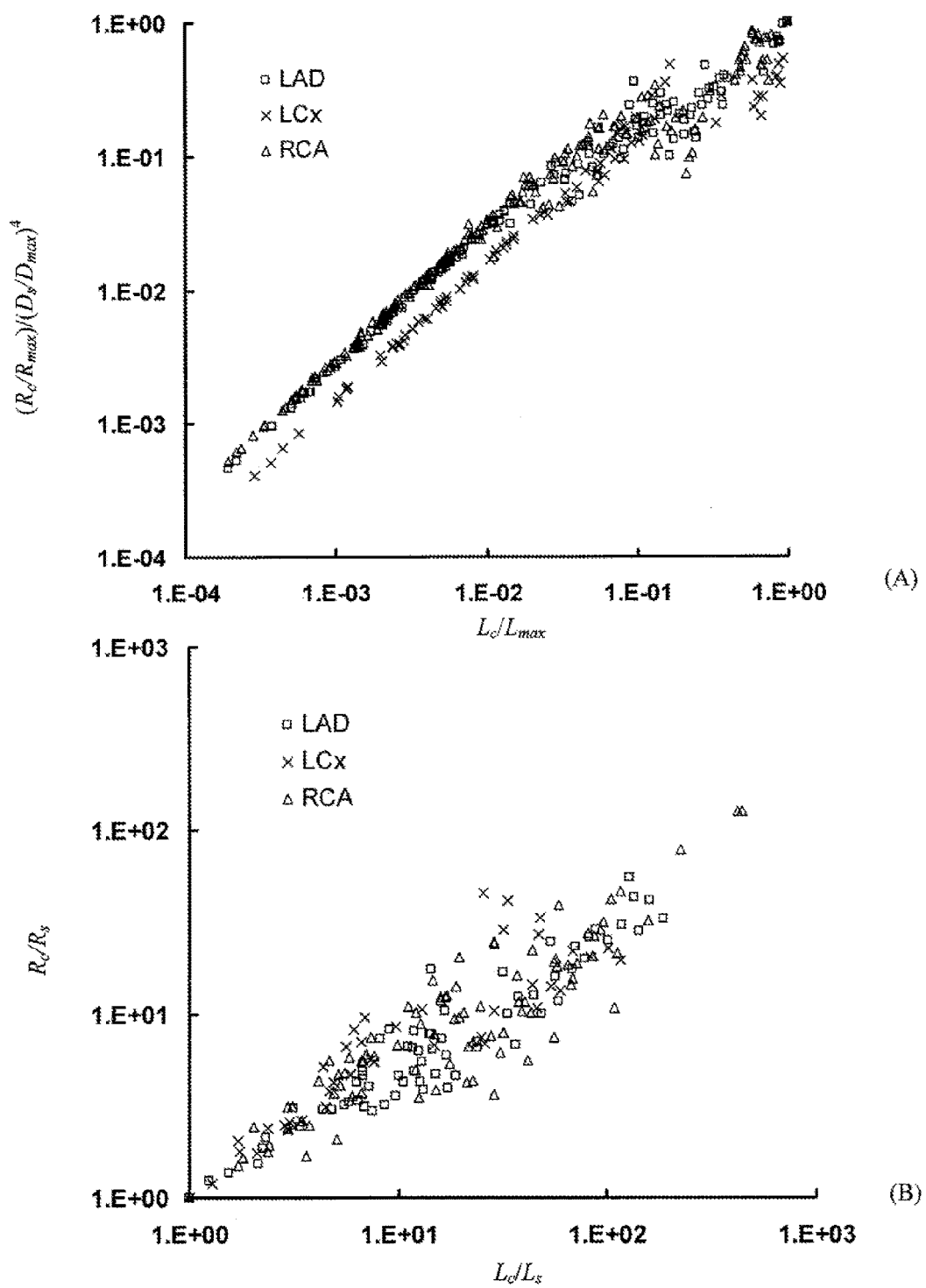
FIG. 8A shows a relationship between resistance and diameter and normalized crown length in the LAD, LCx, and RCA epicardial trees of a pig, respectively, according to at least one embodiment of the present disclosure.
FIG. 8B shows a relationship between resistance and length in the LAD, LCx, and RCA epicardial trees of a pig, respectively, according to at least one embodiment of the present disclosure.

Clinical Implications of Resistance Scaling Law:

The self-similar nature of the structure-function scaling laws in Equations #9, #12 and #13 implies that they can be applied to a partial tree clinically (e.g., a partial tree obtained from an angiogram, computerized tomography, or magnetic resonance imaging). As provided herein, the hypothesis using the LAD, LCx, and RCA epicardial pig trees obtained from casts truncated at 1 mm diameter to mimic the resolution of noninvasive imaging techniques was verified. The good agreement between experiments and theory, as shown in FIG. 8, illustrates that the resistance scaling laws can be applied to partial vascular trees as well as entire trees.

Significance of Resistance Scaling Law:

The novel resistance scaling law (Equations #9 and #12) provides a theoretical and physical basis for understanding the hemodynamic resistance of the entire tree (or a subtree) as well as to provide a rational for clinical diagnosis. The scaling law illustrates the relationship between the structure (tree) and function (resistance), in which the crown resistance is proportional to the crown length and inversely proportional to the fourth power of stem diameter D. The small crown resistance corresponds to a small crown length, thus matching the transport efficiency of the crown. An increase of stem diameter can decrease the resistance, which may contribute to the self scaling of biological transport system. The novel scaling law provides an integration between a single unit and the whole (millions of units) and imparts a rationale for diagnosis of disease processes as well as assessment of therapeutic trials.

The disclosure of the present application provides a novel volume scaling law in a vessel segment and its corresponding distal tree of normal organs and in various species as, for example, $V_c = K_v D_s^{2/3} L_c$, where $V_c$ and $L_c$ are the vascular volume and length, respectively, $D_s$ is the diameter of vessel segment, and $K_v$ is a constant. A novel scaling relation of the disclosure of the present application is validated with available vascular morphometric tree data, and may serve as a control reference to examine the change of blood volume in various organs under different states using conventional imaging. A novel scaling law of the disclosure of the present application is bather validated through diameter-length, volume-length, flow-diameter, and volume-diameter scaling relations, derived based on a minimum energy hypothesis (15). Hence, the novel volume scaling law of the disclosure of the present application is consistent with a (minimum energy) state of efficient vascular system.

In addition to the foregoing, it is known that $V_c \propto M$ (M is the mass perfused by the stem-crown unit) from the ¾ allometric scaling law, where $V_c$ the crown volume the sum of all vessel volumes in the crown). Therefore, $V_c$ can be represented as follows:

$$V_c = C_v M^{1/4} M^{3/4} \tag{14}$$

where $C_v$ is a volume-mass constant.

There are two scaling relations: stem diameter-mass relation, $D_s \propto M^{3/8}$, wherein $D_s$ is the diameter of stem vessel, and crown length-mass relation, $L_c \propto M^{3/4}$, wherein $L_c$ is the crown length that is defined as the sum of the lengths or substantially all of the lengths of each vessel in the crown).

From $D_s = C_d M^{3/8}$, $L_c = C_l M^{3/4}$, and Equation #14, one may obtain:

$$V_c = C_v M^{1/4} M^{3/4} = C_v \left(\frac{D_s}{C_d}\right)^{2/3} \frac{L_c}{C_l} = K_v D_s^{2/3} L_c \tag{15}$$

where $K_v = C_v/(C_d^{2/3} C_l)$ is a constant. Since Equation #15 is applicable to any stem-crown unit, one may obtain $V_{max} = K_v D_{max}^{2/3} L_{max}$, so that $$K_v = \frac{V_{max}}{D_{max}^{2/3} L_{max}},$$

where $D_{max}$, $L_{max}$, and $V_{max}$ correspond to the most proximal stem diameter, the cumulative vascular length of entire tree, and the cumulative vascular volume of entire tree, respectively. Equation #15 can also be made non-dimensional as:

$$\left(\frac{V_c}{V_{max}}\right) = \left(\frac{D_s}{D_{max}}\right)^{\frac{2}{3}} \left(\frac{L_c}{L_{max}}\right) \tag{16}$$

Morphometry of Vascular Trees.

The volume scaling law of the disclosure of the present application is validated in the asymmetric entire coronary arterial tree reconstructed in pig hearts through the growth algorithm based on measured morphometric data. Furthermore, the asymmetric epicardial coronary arterial trees with vessel diameter greater than 1 mm were used to validate the scaling laws in partial vascular trees to mimic the resolution of medical imaging.

Symmetric vascular trees of many organs down to the smallest arterioles were used to verify the proposed structure-function scaling law, which were constructed in the Strahler system, based on the available literature. The arterial and/or venous trees from the various species were obtained as previously referenced herein.

Data Analysis.

All scaling relations Equations #16 and #29-32) can be represented by a form of the type:

$$Y = A \cdot X^B \quad (17)$$

where X and Y are defined such that A and B should have theoretical values of unity for Equation #16. X and Y are defined as $$\left(\frac{D_s}{D_{max}}\right)^{\frac{2}{3}} \left(\frac{L_c}{L_{max}}\right) \text{ and } \left(\frac{V_c}{V_{max}}\right),$$

respectively. For Equations #29-32, X and Y are defined as $$\left(\frac{L_c}{L_{max}}\right) \text{ and } \left(\frac{D_s}{D_{max}}\right); \left(\frac{L_c}{L_{max}}\right) \text{ and } \left(\frac{V_c}{V_{max}}\right); \text{ and}$$

$$\left(\frac{D_s}{D_{max}}\right) \text{ and } \left(\frac{Q_s}{Q_{max}}\right); \left(\frac{D_s}{D_{max}}\right) \text{ and } \left(\frac{V_c}{V_{max}}\right);$$

respectively.

A nonlinear regression was then used to calculate A with B constrained to 3/7, 12/7, 2 1/3 and 3 for Equations #29-32, respectively. The nonlinear regression uses the Marquardt-Levenberg algorithm to find the parameter, A, for the variables X and Y to provide the "best fit" between the equation and the data. In Equations #16 and #29-32, the parameter A should have a theoretical value of one.

Results.

Asymmetric Tree Model.

Figure 12:
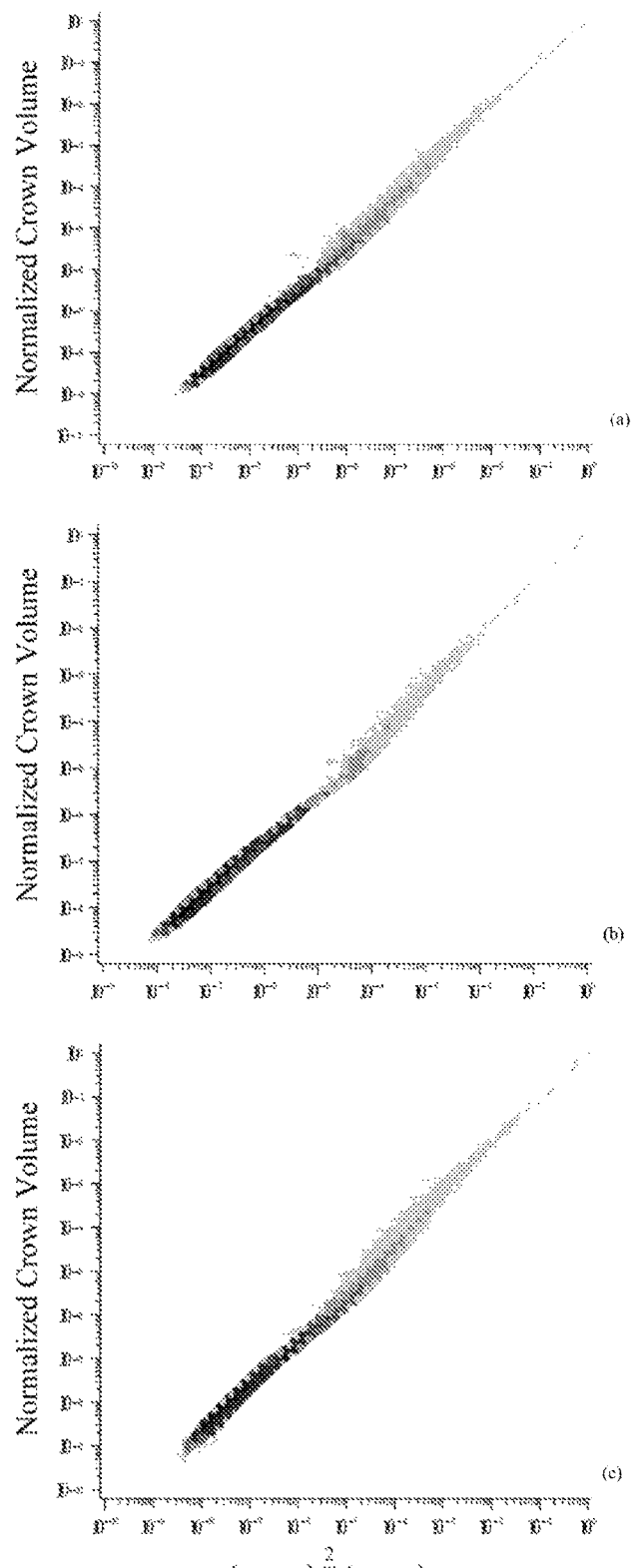
FIGS. 12A-12C show relations between diameter and length and normalized crown volume in the LAD, LCx, and RCA trees of a pig, respectively, according to at least one embodiment of the present disclosure.
Figure 13:
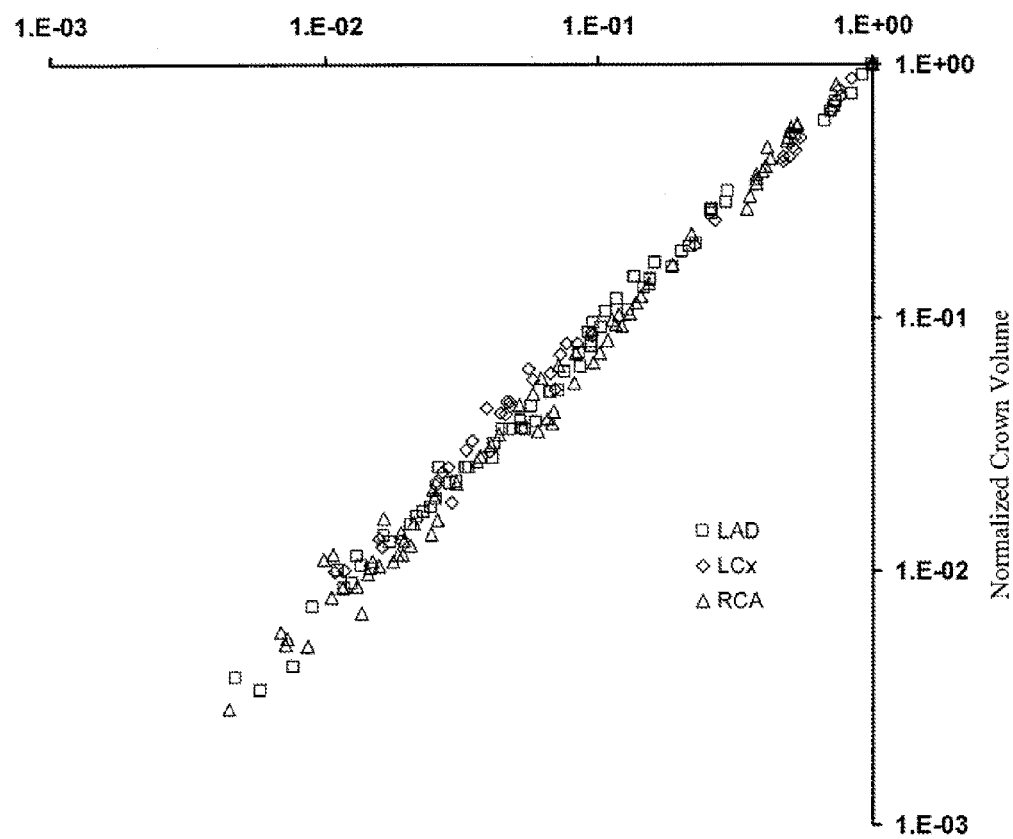
FIG. 13 shows a relation between diameter and length and normalized crown volume in the LAD, LCx, and RCA epicardial trees of a pig, respectively, according to at least one embodiment of the present disclosure.

The disclosure of the present application provides a novel volume scaling law that relates the crown volume to the stem diameter and crown length in Equations #15 and #16. The validity of Equations #15 and #16 were examined in the asymmetric entire (down to the pre-capillary vessel segments) and epicardial (vessel diameter≥1 mm) LAD, LCx, and RCA trees of pig, as shown in FIGS. 12 and 13, respectively. FIG. 12 shows a relation between $$\left(\frac{D_s}{D_{max}}\right)^{\frac{2}{3}} \left(\frac{L_c}{L_{max}}\right)$$

and normalized crown volume in the entire asymmetric (a) LAD, (b) LCx, and (c) RCA trees of pig, which include 946,937, 571,383, and 836,712 vessel segments, respectively. The entire tree data are presented as log-log density plots showing the frequency of data because of the enormity of data points, i.e., darkest shade reflects highest frequency or density and the lightest shade reflects the lowest frequency. FIG. 13 shows a relation between $$\left(\frac{D_s}{D_{max}}\right)^{\frac{2}{3}} \left(\frac{L_c}{L_{max}}\right)$$

and normalized crown volume in the asymmetric LAD, LCx, and RCA epicardial trees of pig with vessel diameter larger than 1 mm, which include 66, 42, and 71 vessel segments, respectively.

As shown in FIG. 9, exponent B is determined from a least-square fit, and parameter A is calculated by the nonlinear regression with the exponent B constrained to one. Both B and A for the entire asymmetric and partial trees show agreement with the theoretical value of one. For the table shown in FIG. 9, Parameters B (obtained from least-square fits) and A (obtained from nonlinear regression with B constrained to one) in the asymmetric entire coronary trees and in the corresponding epicardial trees with vessel diameter >1 mm when Equation #16 is represented by Equation #17, where independent variables $$X = \left(\frac{D_s}{D_{max}}\right)^{\frac{2}{3}} \left(\frac{L_c}{L_{max}}\right) \text{ and } Y = \left(\frac{V_c}{V_{max}}\right),$$

as shown in FIGS. 12 and 13. SE and $R^2$ are the standard error and correlation coefficient, respectively.

Symmetric Tree Model.

Figure 14:
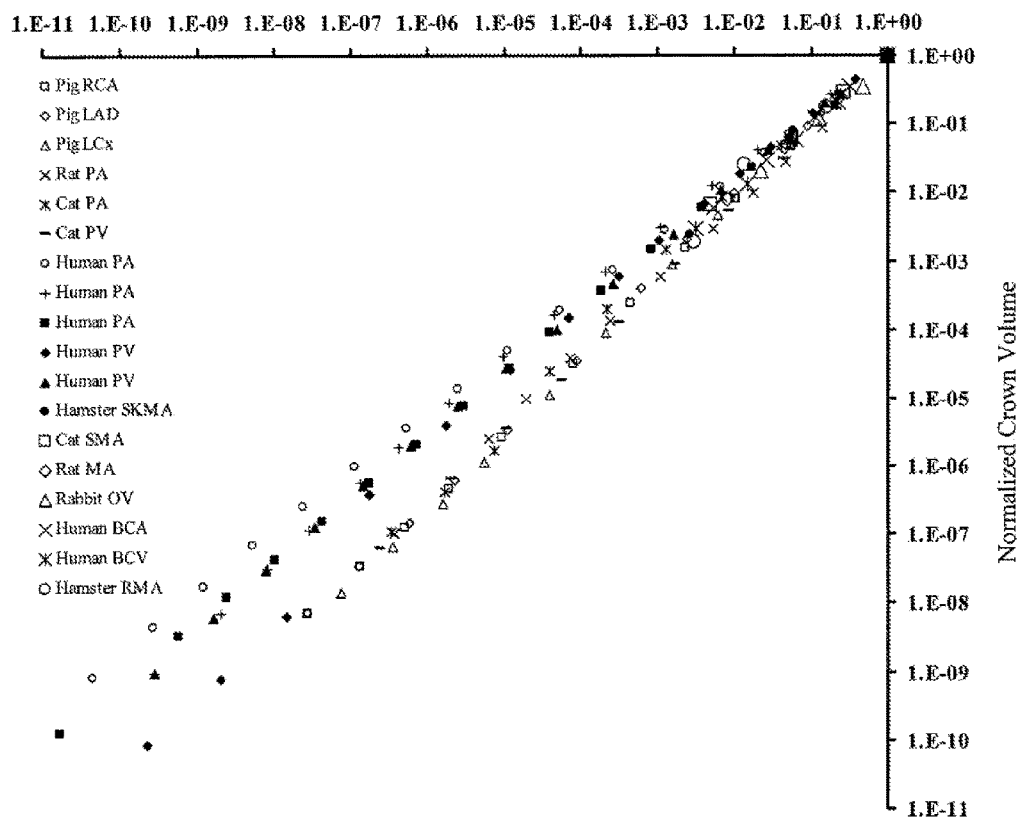
FIG. 14 shows a relation between diameter and length and normalized crown volume in the symmetric vascular tree for various organs and species, according to at least one embodiment of the present disclosure.

Equation #16 is also validated in symmetric trees for various organs and species, as shown in FIG. 14. FIG. 14 shows a relation between $$\left(\frac{D_s}{D_{max}}\right)^{\frac{2}{3}} \left(\frac{L_c}{L_{max}}\right)$$

and normalized crown volume in the symmetric vascular tree for various organs and species (21-33), corresponding to the table shown in FIG. 10. Parameters B and A are listed in the table shown in FIG. 10, which have a mean±SD value of 1.02±0.02 and 1.00±0.01, respectively, by averaging over various organs and species. These parameters are in agreement with the theoretical value of one. Furthermore, Equation #15 implies that $$K_v = \frac{V_{max}}{D_{max}^{2/3} L_{max}},$$

which can be compared with the regression-derived value. For the table shown in FIG. 10, parameters B (obtained from least-square fits) and A (obtained from nonlinear regression with B constrained to one) in various organs when Equation #16 is represented by Equation #17, where independent variables $$X = \left(\frac{D_s}{D_{max}}\right)^{\frac{2}{3}} \left(\frac{L_c}{L_{max}}\right) \text{ and } Y = \left(\frac{V_c}{V_{max}}\right),$$

as shown in FIG. 14. SE and $R^2$ are the standard error and correlation coefficient, respectively.

Figure 15:
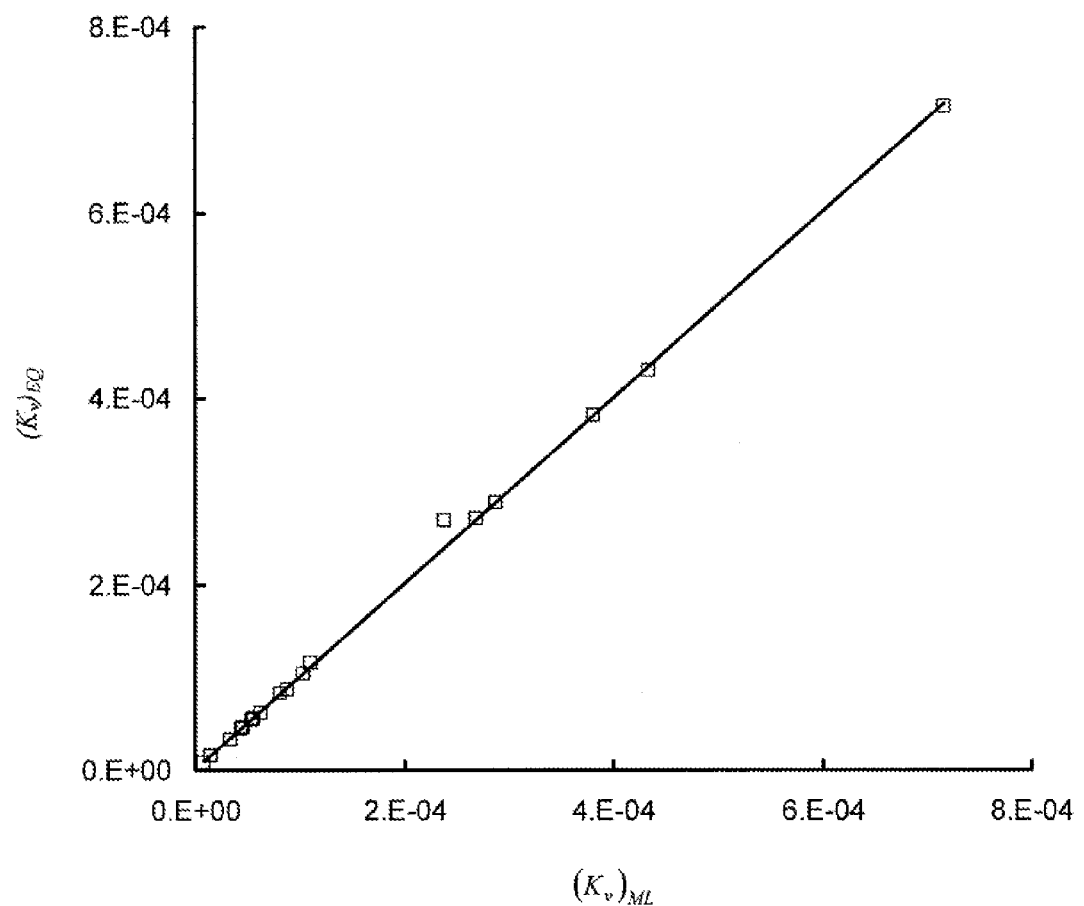
FIG. 15 shows a comparison of data from nonlinear regression and an equation of the present disclosure; according to at least one embodiment of the present disclosure.

FIG. 15 shows a comparison of $(K_v)_{ML}$ obtained from the nonlinear regression of anatomical data and $(K_v)_{EQ}$ calculated from Equations #15 and #16. A least-square fit results in a relation of the form: $(K_v)_{EQ} = 0.998 \, (K_v)_{ML}$ ($R^2 = 0.999$).

Scaling Relations.

To further validate the novel volume scaling law of the disclosure of the present application, a number of scaling relations between morphological and hemodynamic parameters are provided below. For these relations, parameter A has the theoretical value of one as exponent B has a theoretical value of 3/7, 12/7, 21/3 and 3 for diameter-length relation, volume-length relation, flow-diameter relation, and volume-diameter relation in Equations #29-32, respectively. The values for A are listed in the table shown in FIG. 11 as determined from nonlinear regression. These values, averaged over various organs and species, have mean±SD values of 1.01±0.07, 1.00±0.02, 0.99±0.05, and 0.99±0.03 for Equations #29-32, respectively. The agreement of data with theoretical predictions is excellent as demonstrated by the data referenced herein. For the table shown in FIG. 11, the parameter A obtained from nonlinear regression in various organs when Equations #29-32 (diameter-length, volume-length, flow-diameter, and volume-diameter relations, respectively) are represented by Equation #17. The exponent B is constrained to, 3/7, 12/7, 21/3, and 3 for Equations #29-32, respectively. SE and $R^2$ are the standard error and correlation coefficient, respectively.

Volume Scaling Law.

Many structural and functional features are found to have a power-law (scaling) relation to body size, metabolic rates, etc. Previous studies showed several scaling relations connecting structure with function. A novel volume scaling relation of the disclosure of the present application has been demonstrated and validated, which relates the crown volume to the stem diameter and crown length.

Clinical techniques (e.g., indicator and dye-dilution method) have been used to predict blood volume for decades. The blood volume varies significantly with body size such that it is difficult to evaluate the change of blood volume in patients because of lack of reference. Although Feldschuh and Enson (Prediction of the normal blood volume: relation of blood volume to body habitus. *Circulation.* 56: 605-612 (1977) used the metropolitan life height and weight tables to determine an ideal weight as an approximate reference, this approach lacks a physical or physiological basis for calculating normal blood volume. The novel volume scaling law of the disclosure of the present application may establish the signature of "normality" and deviation thereof may be indicative of pathology.

The remodeling of intravascular volume may be physiologic during normal growth, exercise, or pregnancy. It may also be pathological, however, in hypertension, tumor, or diffuse vascular diseases. Diffuse vascular disease is difficult to quantify because the normal reference does not exist. The disclosure of the present application shows that the volume scaling law holds in the coronary epicardial trees (vessel diameter>1 mm), as shown in FIG. 13 and the table shown in FIG. 9. Such data on coronaries or other vascular trees are available, for example, by angiography. CT, or MRI. Hence, the novel volume scaling law of the disclosure of the present application can serve to quantify diffuse vascular disease in various organs clinically.

Comparison with ZKM Model.

As referenced herein, vascular trees provide the channels to transport fluid to different organs. The optimal design of vascular tree is required to minimize energy losses. Although many theoretical approaches are proposed to explain the design of vascular tree, the "Minimum Energy Hypothesis" may be the most validated hypothesis. The ZKM model, based on the minimum energy hypothesis, predicted the exponents $$\chi = \frac{3\varepsilon' - 2}{4(\varepsilon' + 1)}, \beta = \frac{5}{\varepsilon' + 1}, \delta = \frac{4(\varepsilon' + 1)}{3\varepsilon' - 2}$$

for diameter-length, volume-length, and flow-diameter relations, respectively, where the parameter $\varepsilon'$ in the exponents is the ratio of maximum metabolic to viscous power dissipation for a given tree. Based on Equations #15 and #16 of the disclosure of the present application, the corresponding exponents $\chi=3/7$, $\beta=12/7$, and $\delta 21/3$ are shown. With the respective $\varepsilon'$, the mean values over all organs and species are 0.43±0.02, 1.28±0.09, and 2.33±0.11 for exponents $\chi$, $\beta$, $\delta$, respectively, which agrees well with the present predicted information, i.e., 3/7≈0.43, 12/7≈1.29, and 21/3≈22.33. Furthermore, ZKM model shows the mean±SD value of 2.98±0.34 for volume-diameter relation with the respective $\varepsilon'$, which is consistent with the exponent value of 3 in Equation #32. This provides further validation for the proposed volume scaling law of the disclosure of the present application.

Comparison with 3/4-Power Law.

West et al. (A general model for the origin of allometric scaling laws in biology. *Science.* 276:122-126 (1997)) proposed the 3/4-power scaling law (WBE model) to describe how essential materials are transported in the vascular tree. The WBE model predicts the following scaling relations: $Q_s \propto M^{3/4}$, $V_c \propto M$, and $D_s \propto M^{3/8}$. If the first and third relations are combined, one obtains the flow-diameter relation with an exponent of $\delta=2$, which implies that the flow velocity is constant from the large artery to the smallest arterioles. This is in contradiction with experimental measurements.

If the second and third relations are combined, one obtains the volume-diameter relation as:

$$\left(\frac{V_c}{V_{max}}\right) = \left(\frac{D_s}{D_{max}}\right)^{\frac{8}{3}} = \left(\frac{A_s}{A_{max}}\right)^{\frac{4}{3}},$$

such that the area-volume relation is $$\left(\frac{A_s}{A_{max}}\right) = \left(\frac{V_c}{V_{max}}\right)^{\frac{3}{4}},$$

where $A_s$ and $A_{max}$ are the stem area and the most proximal area, respectively. These WBE predictions differ from the experimental observation:

$$\left(\frac{A_s}{A_{max}}\right) = \left(\frac{V_c}{V_{max}}\right)^{\frac{2}{3}}.$$

When the cost function in Equation #22 is minimized, one obtains the exponent $\delta=21/3$, which agrees well with the anatomical data (as shown in the table of FIG. 10). The area-volume relation $$\left(\left(\frac{A_s}{A_{max}}\right) = \left(\frac{V_c}{V_{max}}\right)^{\frac{2}{3}}\right)$$

obtained from Equation #32 is consistent with the experimental measurements.

There is additional departure of the present model from that of WBE. Equation #30 and $V_c \propto M$ lead to the following relation:

$$L_c \propto M^{7/9} \quad (18)$$

From Equations #18 and #25, the following relation may be identified:

$$Q_s \propto M^{7/9} \quad (19)$$

From Equation #32 and $V_c \propto M$, the following relation may be identified:

$$D_s \propto M^{1/3} \quad (20)$$

Although these scaling relations are different from the WBE model, $V_c \propto D_s^{2/3} L_c$ (Equations #18 and #20 and $V_c \propto M$) is still obtained, which further supports the validity of Equations #15 and #16. Equation #19 implies that the ¾-power scaling law ($Q_s \propto M^{3/4=0.75}$) should be ⅞-power scaling law ($Q_s \propto M^{7/9=0.78}$). A least-square fit of $Q_s$–M data has an exponent value of 0.78 ($R^2 = 0.985$), which is consistent with the ⅞-power scaling law.

Optimal Cost Function.

From Equations #26 and #28, the non-dimensional cost function can be written as follows:

$$f_c = \frac{1}{6} \frac{(L_c/L_{max})^3}{(D_s/D_{max})^4} + \left(\frac{D_s}{D_{max}}\right)^{2/3} \left(\frac{L_c}{L_{max}}\right) \quad (21)$$

This is the minimum cost of maintaining an optimal design of a vascular tree under homeostasis. From the structure-function scaling relations (Equation #29), $$\frac{(L_c/L_{max})^3}{(D_s/D_{max})^4} = \left(\frac{L_c}{L_{max}}\right)^{1\frac{2}{7}} \text{ and } \left(\frac{D_s}{D_{max}}\right)^{2/3}\left(\frac{L_c}{L_{max}}\right) = \left(\frac{L_c}{L_{max}}\right)^{1\frac{2}{7}},$$

one may obtain $$\frac{(L_c/L_{max})^3}{(D_s/D_{max})^4} = \left(\frac{D_s}{D_{max}}\right)^{2/3}\left(\frac{L_c}{L_{max}}\right).$$

The power required to overcome the viscous drag of blood flow (second term in Equation #21) is one sixth of the power required to maintain the volume of blood (third term in Equation #21). This expression implies that most of energy is dissipated for maintaining the metabolic cost of blood, which is proportional to the metabolic dissipation.

Additional Validation of Volume Scaling Law.

From Equations #15 and 16, the disclosure of the present application identifies the cost function for a crown, $F_c$, consistent with previous formulation:

$$F_c = Q_s \cdot \Delta P_c + K_m V_c = Q_s^2 \cdot R_c + K_m K_v D_s^{2/3} L_c \quad (22)$$

where $Q_s$ and $\Delta P_c = Q_s \cdot R_c$ are the flow rate through the stem and the pressure drop in the distal crown, respectively, and $K_m$ is a metabolic constant of blood in a crown. The resistance of a crown has been identified as $$R_c = K_c \frac{L_c}{D_s^4},$$

where $K_c$ is a constant. The cost function of a crown tree in Equation #22 can be written as $$F_c = Q_s^2 \cdot R_c + K_m K_v D_s^{2/3} L_c = K_c Q_s^2 \frac{L_c}{D_s^4} + K_m K_v D_s^{2/3} L_c \quad (23)$$

Equation #23 can be normalized by the metabolic power requirements of the entire tree of interest, $K_m V_{max} = K_m K_v D_{max}^{2/3} L_{max}$, to obtain:

$$f_c = \frac{F_c}{K_m K_v D_{max}^{2/3} L_{max}} = \quad (24)$$

$$\frac{Q_{max}^2 R_{max}}{K_m K_v D_{max}^{2/3} L_{max}} \left(\frac{Q_s}{Q_{max}}\right)^2 \cdot \frac{(L_c/L_{max})}{(D_s/D_{max})^4} + \left(\frac{D_s}{D_{max}}\right)^{2/3}\left(\frac{L_c}{L_{max}}\right)$$

where $f_c$ is the non-dimensional cost function. A previous analysis shows:

$$Q_s = K_Q L_c \Rightarrow \frac{Q_s}{Q_{max}} = \frac{L_c}{L_{max}} \quad (25)$$

where $K_Q$ is a flow-crown length constant. When Equation #25 is applied to Equation #24, the dimensionless cost function can be written as:

$$f_c = \frac{Q_{max}^2 R_{max}}{K_m K_v D_{max}^{2/3} L_{max}} \cdot \frac{(L_c/L_{max})^3}{(D_s/D_{max})^4} + \left(\frac{D_s}{D_{max}}\right)^{2/3}\left(\frac{L_c}{L_{max}}\right) \quad (26)$$

Similar to Murray's law, the cost function may be minimized with respect to diameter at a fixed $L_c/L_{max}$ to obtain the following:

$$\frac{\partial f_c}{\partial\left(\frac{D_s}{D_{max}}\right)} = 0 \Rightarrow \frac{(-4)Q_{max}^2 R_{max}}{K_m K_v D_{max}^{2/3} L_{max}} \cdot \frac{(L_c/L_{max})^3}{(D_s/D_{max})^5} = \quad (27)$$

$$-\left(\frac{2}{3}\right)\left(\frac{D_s}{D_{max}}\right)^{\frac{2}{3}-1}\left(\frac{L_c}{L_{max}}\right) \Rightarrow \frac{6Q_{max}^2 R_{max}}{K_m K_v D_{max}^{2/3} L_{max}} \cdot \left(\frac{L_c}{L_{max}}\right)^2 = \left(\frac{D_s}{D_{max}}\right)^{4+\frac{2}{3}}$$

Equation #27 applies to any stem-crown unit. When $L_c = L_{max}$ and $D_s = D_{max}$ in Equation #27, one may obtain:

$$\frac{6Q_{max}^2 R_{max}}{K_m K_v D_{max}^{2/3} L_{max}} = 1 \Rightarrow \frac{Q_{max}^2 R_{max}}{K_m K_v D_{max}^{2/3} L_{max}} = \frac{1}{6} \quad (28)$$

Therefore, Equation #28 can be written as:

$$\left(\frac{D_s}{D_{max}}\right) = \left(\frac{L_c}{L_{max}}\right)^{\frac{3}{7}} \quad (29)$$

From Equations #16 and #29, one may obtain:

$$\left(\frac{V_c}{V_{max}}\right) = \left(\frac{L_c}{L_{max}}\right)^{1\frac{2}{7}} \quad (30)$$

From Equations #25 and #29, one may find:

$$\left(\frac{Q_s}{Q_{max}}\right) = \left(\frac{D_s}{D_{max}}\right)^{2\frac{1}{3}} \quad (31)$$

where $Q_{max}$ is the flow rate through the most proximal stem. From Equations #29 and #30, one may obtain:

$$\left(\frac{V_c}{V_{max}}\right) = \left(\frac{D_s}{D_{max}}\right)^3 \quad (32)$$

Equations #29-32 are the structure-function scaling relations in the vascular tree, based on the "Minimum Energy Hypothesis". Equations #29, #30, and #32 represent the diameter-length, volume-length, and volume-diameter relations, respectively and Equation #31 represents the general Murray's law in the entire tree.

The disclosure of the present application also relates to the design and fabrication of micro-fluidic chambers for use in research and development, thereby designing a chamber that maximizes flow conditions while minimizing the amount of material needed to construct the chamber. Many other uses are also possible and within the scope of the disclosure of the present application.

The foregoing disclosure of the exemplary embodiments of the present application has been presented for purposes of illustration and description and can be further modified within the scope and spirit of this disclosure. It is not intended to be exhaustive or to limit the present disclosure to the precise forms disclosed. This application is therefore intended to cover any variations, uses, or adaptations of a device, system and method of the present application using its general principles. Further, this application is intended to cover such departures from the present disclosure as may come within known or customary practice in the art to which this system of the present application pertains. Many variations and modifications of the embodiments described herein will be apparent to one of ordinary skill in the art in light of the above disclosure. The scope of the present disclosure is to be defined only by the claims appended hereto, and by their equivalents.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

The invention claimed is:

1. A method for diagnosing and treating disease in a patient's biological tree, the method comprising the steps of:
   using a processor to produce an image showing a vasculature of at least part of a patient's biological tree, wherein the processor is operably connected to a storage medium capable of receiving and storing the image;
   calculating patient resistance based upon at least a length of a patient vessel portion and a diameter of a patient stem vessel proximal to the vessel crown from the patient's biological tree image;
   obtaining a model biological tree image and comparing the calculated patient resistance to a calculated model resistance calculated from the model biological tree image to determine the extent of vessel and/or organ disease; and
   treating the patient based on the determined extent of vessel and/or organ disease.

2. The method of claim 1, wherein the calculated model resistance is based upon at least a length of a model vessel portion and a diameter of a model stem vessel proximal to the vessel crown from the model biological tree image.

3. The method of claim 1, wherein the patient resistance is a resistance of a stem segment, and wherein the length of the patient vessel portion is a length of a stem.

4. The method of claim 1, wherein the patient resistance is a resistance of a crown, and wherein the length of the patient vessel portion is a crown length.

5. The method of claim 1, wherein the patient resistance is a total resistance of the biological tree, and wherein the length of the patient vessel portion is a cumulative biological tree vessel length.

6. The method of claim 1, wherein the patient resistance is the resistance of blood within a vessel portion.

7. The method of claim 1, wherein the patient vessel portion comprises a vessel selected from the group consisting of a blood vessel, a bile duct, a lung, and a neuron.

8. The method of claim 1, wherein the patient resistance is the resistance of a gas within a vessel portion.

9. The method of claim 8, wherein the gas comprises breathable air, and wherein the vessel portion comprises a portion of a lung.

10. The method of claim 1, wherein the extent of vessel and/or organ disease is indicative of a disease selected from the group consisting of diffuse coronary artery disease, hypertension, atherosclerosis, heart failure, myocardial ischemia, myocardial infarction, an edematous disorder, and postural tachycardia syndrome.

11. A method for diagnosing and treating disease in a patient's biological tree, the method comprising the steps of:
   using a processor to produce an image showing a vasculature of at least part of a patient's biological tree, wherein the processor is operably connected to a storage medium capable of receiving and storing the image;
   calculating patient cumulative crown volume based upon at least a diameter of a patient stem segment and a length of a patient stem segment from the patient's biological tree image;
   obtaining a model biological tree image and comparing the calculated patient cumulative crown volume to a calculated model cumulative crown volume calculated from the model biological tree image to determine the extent of vessel and/or organ disease; and
   treating the patient if the determined extent of the vessel and/or organ disease indicates an inefficiency of the vasculature.

12. The method of claim 11, wherein the calculated model cumulative crown volume is based upon at least a diameter of a model stem segment and a length of a model stem segment from the model biological tree image.

13. The method of claim 11, wherein the step of comparing the calculated patient cumulative crown volume to the calculated model cumulative crown volume is performed by graphically comparing calculated model cumulative crown volume data to calculated model cumulative crown volume data to determine the extent of vessel and/or organ disease by identifying one or more graphical differences between said data.

14. The method of claim 11, wherein the step of comparing the calculated patient cumulative crown volume to the calculated model cumulative crown volume is performed by comparing calculated model cumulative crown volume data to calculated model cumulative crown volume data in table form to determine the extent of vessel and/or organ disease by identifying one or more numerically calculated differences between said data.

15. The method of claim 11, wherein the method further comprises the steps of:
identifying a most proximal patient stem diameter from the patient's biological tree image;
identifying a patient's cumulative biological tree vessel length from the patient's biological tree image; and
calculating a patient's cumulative biological tree volume of the patient's biological tree based upon at least the most proximal patient stem diameter and the patient's cumulative biological tree vessel length.

16. The method of claim 15, further comprising the step of determining a structure-function scaling relation, wherein the structure-function scaling relation comprises a first component and a second component, or a mathematical equivalent thereof.

17. The method of claim 16, further comprising the step of determining a non-dimensional structure-function scaling relation, wherein the non-dimensional structure-function scaling relation comprises a first component, a second component, and a third component, or a mathematical equivalent thereof.

18. The method of claim 11, wherein the calculated patient's cumulative crown volume provides information useful for a diagnosis of a disease.

19. The method of claim 11, wherein the extent of vessel and/or organ disease is indicative of a disease selected from the group consisting of diffuse coronary artery disease, hypertension, atherosclerosis, heart failure, myocardial ischemia, myocardial infarction, an edematous disorder, and postural tachycardia syndrome.

20. A system for diagnosing disease in a patient's biological tree, the system comprising:
a processor;
a storage medium operably connected to the processor, the storage medium capable of receiving and storing data relative of measurements from a vasculature of a vessel;
wherein the processor is operable to:
produce an image showing a vasculature of at least part of a patient's biological tree, the image to be received and stored in the storage medium;
calculate patient resistance based upon at least a length of a patient vessel portion and a diameter of a patient stem vessel proximal to the vessel crown from the patient's biological tree image; and
obtain a model biological tree image and compare the calculated patient resistance to a calculated model resistance calculated from the model biological tree image to determine the extent of vessel and/or organ disease.

* * * * *